United States Patent
Deutsch et al.

(10) Patent No.: US 8,597,597 B2
(45) Date of Patent: *Dec. 3, 2013

(54) PICOLITER WELL HOLDING DEVICE AND METHOD OF MAKING THE SAME

(75) Inventors: Mordechai Deutsch, Moshav Olesh Doar-Na Lev HaSharon (IL); Assaf Deutsch, Tzfaria (IL)

(73) Assignee: Seng Enterprises Ltd., Larnaca (CY)

( * ) Notice: Subject to any disclaimer, the term of this patent is extended or adjusted under 35 U.S.C. 154(b) by 89 days.

This patent is subject to a terminal disclaimer.

(21) Appl. No.: 12/742,730

(22) PCT Filed: Nov. 13, 2008

(86) PCT No.: PCT/IL2008/001492
§ 371 (c)(1),
(2), (4) Date: May 13, 2010

(87) PCT Pub. No.: WO2009/063462
PCT Pub. Date: May 22, 2009

(65) Prior Publication Data

US 2010/0247386 A1    Sep. 30, 2010

Related U.S. Application Data

(63) Continuation of application No. 11/940,996, filed on Nov. 15, 2007, now Pat. No. 7,888,110, which is a continuation-in-part of application No. 10/561,839, filed as application No. PCT/IL2004/000571 on Jun. 27, 2004, said application No. 11/940,996 is a continuation-in-part of application No. PCT/IL2006/001487, filed on Dec. 26, 2006.

(60) Provisional application No. 61/006,130, filed on Dec. 26, 2007, provisional application No. 60/544,357, filed on Feb. 17, 2004, provisional application No. 60/544,356, filed on Feb. 17, 2004, provisional application No. 60/517,073, filed on Nov. 5, 2003, provisional application No. 60/517,084, filed on Nov. 5, 2003, provisional application No. 60/488,408, filed on Jul. 21, 2003, provisional application No. 60/482,437, filed on Jun. 26, 2003, provisional application No. 60/754,216, filed on Dec. 28, 2005.

(51) Int. Cl.
*B01L 3/00* (2006.01)

(52) U.S. Cl.
USPC .................................................. 422/553

(58) Field of Classification Search
USPC .................................................. 422/553
See application file for complete search history.

(56) References Cited

U.S. PATENT DOCUMENTS

| | | |
|---|---|---|
| 3,558,387 A | 1/1971 | Bassemir et al. |
| 4,072,578 A | 2/1978 | Cady et al. |

(Continued)

FOREIGN PATENT DOCUMENTS

| | | |
|---|---|---|
| DE | 4132379 | 4/1993 |
| EP | 0059297 | 9/1982 |

(Continued)

OTHER PUBLICATIONS

Communication Pursuant to Article 94(3) EPC Dated Aug. 5, 2010 From the European Patent Office Re. Application No. 05757567.2.

(Continued)

*Primary Examiner* — Lore Jarrett

(57) ABSTRACT

Described herein are embossing methods for forming pico liter well arrays (and other structures), arrangements of such pico liter well arrays, for example, in arrays of pico liter well areas, and methods of forming templates for such embossing. Also described as wells with a refractive index similar to that of an aqueous medium used for supporting cells in the wells.

15 Claims, 11 Drawing Sheets

(56) References Cited

U.S. PATENT DOCUMENTS

| | | |
|---|---|---|
| 4,207,554 A | 6/1980 | Resnick et al. |
| 4,308,351 A | 12/1981 | Leighton et al. |
| 4,684,538 A | 8/1987 | Klemarczyk |
| 4,716,101 A | 12/1987 | Thompson |
| 4,729,949 A | 3/1988 | Weinreb et al. |
| 4,839,280 A | 6/1989 | Banes |
| 4,894,343 A | 1/1990 | Tanaka et al. |
| 4,895,805 A | 1/1990 | Sato et al. |
| 5,043,082 A | 8/1991 | Hermann, Jr. et al. |
| 5,059,266 A | 10/1991 | Yamane et al. |
| 5,153,136 A | 10/1992 | Vandenburgh |
| 5,204,055 A | 4/1993 | Sachs et al. |
| 5,272,081 A | 12/1993 | Weinreb |
| 5,324,591 A | 6/1994 | Georger et al. |
| 5,395,588 A | 3/1995 | North, Jr. et al. |
| 5,428,451 A | 6/1995 | Lea et al. |
| 5,506,141 A | 4/1996 | Weinreb et al. |
| 5,525,800 A | 6/1996 | Sanghera et al. |
| 5,612,184 A | 3/1997 | Rosson |
| 5,627,045 A | 5/1997 | Bochner et al. |
| 5,650,323 A | 7/1997 | Root et al. |
| 5,707,869 A | 1/1998 | Wolf et al. |
| 5,744,366 A | 4/1998 | Kricka et al. |
| 5,854,684 A | 12/1998 | Stabile et al. |
| 5,905,031 A | 5/1999 | Kuylen et al. |
| 5,910,287 A | 6/1999 | Cassin et al. |
| 6,025,129 A | 2/2000 | Nova et al. |
| 6,027,695 A | 2/2000 | Oldenburg et al. |
| 6,046,426 A | 4/2000 | Jeantette et al. |
| 6,048,723 A | 4/2000 | Banes |
| 6,066,285 A | 5/2000 | Kumar |
| 6,103,479 A | 8/2000 | Taylor |
| 6,117,612 A | 9/2000 | Halloran et al. |
| 6,206,672 B1 | 3/2001 | Grenda |
| 6,228,437 B1 | 5/2001 | Schmidt |
| 6,238,614 B1 | 5/2001 | Yang et al. |
| 6,315,940 B1 | 11/2001 | Nisch et al. |
| 6,329,195 B1 | 12/2001 | Pfaller |
| 6,333,192 B1 | 12/2001 | Petitte et al. |
| 6,338,964 B1 | 1/2002 | Matanguihan et al. |
| 6,342,384 B1 | 1/2002 | Chung et al. |
| 6,344,354 B1 | 2/2002 | Webster et al. |
| 6,345,115 B1 | 2/2002 | Ramm et al. |
| 6,372,494 B1 | 4/2002 | Naughton et al. |
| 6,376,148 B1 | 4/2002 | Liu et al. |
| 6,377,721 B1 | 4/2002 | Walt et al. |
| 6,378,527 B1 | 4/2002 | Hungerford et al. |
| 6,383,810 B2 | 5/2002 | Fike et al. |
| 6,403,369 B1 | 6/2002 | Wood |
| 6,410,309 B1 | 6/2002 | Barbera-Guillem et al. |
| 6,413,680 B1 | 7/2002 | Watanabe et al. |
| 6,413,744 B1 | 7/2002 | Morris et al. |
| 6,413,746 B1 | 7/2002 | Field |
| 6,416,642 B1 | 7/2002 | Alajoki et al. |
| 6,455,310 B1 | 9/2002 | Barbera-Guillem et al. |
| 6,465,000 B1 | 10/2002 | Kim |
| 6,465,205 B2 | 10/2002 | Hicks, Jr. |
| 6,468,788 B1 | 10/2002 | Marotzki |
| 6,479,252 B1 | 11/2002 | Barbera-Guillem et al. |
| 6,485,690 B1 | 11/2002 | Pfost et al. |
| 6,489,144 B1 | 12/2002 | Lau |
| 6,492,148 B1 | 12/2002 | van Loon et al. |
| 6,492,163 B1 | 12/2002 | Yoo et al. |
| 6,495,340 B2 | 12/2002 | Huberman et al. |
| 6,506,598 B1 | 1/2003 | Andersen et al. |
| 6,511,430 B1 | 1/2003 | Sherar et al. |
| 6,521,182 B1 | 2/2003 | Shartle et al. |
| 6,528,286 B1 | 3/2003 | Ryll |
| 6,544,788 B2 | 4/2003 | Singh |
| 6,555,365 B2 | 4/2003 | Barbera-Guillem et al. |
| 6,569,422 B1 | 5/2003 | van Loon et al. |
| 6,588,586 B2 | 7/2003 | Abasolo et al. |
| 6,589,765 B1 | 7/2003 | Choi et al. |
| 6,593,101 B2 | 7/2003 | Richards-Kortum et al. |
| 6,593,140 B1 | 7/2003 | Field |
| 6,610,516 B1 | 8/2003 | Andersen et al. |
| 6,627,426 B2 | 9/2003 | Biddle et al. |
| 6,632,619 B1 | 10/2003 | Harrison et al. |
| 6,635,448 B2 | 10/2003 | Bucciarelli et al. |
| 6,642,050 B1 | 11/2003 | Goto et al. |
| 6,645,757 B1 | 11/2003 | Okandan et al. |
| 6,649,408 B2 | 11/2003 | Bailey et al. |
| 6,653,124 B1 | 11/2003 | Freeman |
| 6,660,501 B2 | 12/2003 | Field |
| 6,667,034 B2 | 12/2003 | Palsson et al. |
| 6,670,180 B2 | 12/2003 | Block |
| 6,670,184 B2 | 12/2003 | Chiarello et al. |
| 6,673,591 B2 | 1/2004 | Lau |
| 6,686,190 B2 | 2/2004 | Lau |
| 6,689,594 B1 | 2/2004 | Hänni et al. |
| 6,692,961 B1 | 2/2004 | Judd et al. |
| 6,695,765 B1 | 2/2004 | Beebe et al. |
| 6,699,665 B1 | 3/2004 | Kim et al. |
| 6,706,519 B1 | 3/2004 | Kellogg et al. |
| 7,118,910 B2 | 10/2006 | Unger et al. |
| 7,139,415 B2 | 11/2006 | Finkbeiner |
| 7,169,578 B2 | 1/2007 | Wang et al. |
| 7,285,412 B2 | 10/2007 | Casagrande et al. |
| 7,323,305 B2 | 1/2008 | Leamon et al. |
| 7,354,733 B2 | 4/2008 | Bukshpan et al. |
| 7,403,647 B2 | 7/2008 | Deutsch et al. |
| 7,405,071 B2 | 7/2008 | Deutsch |
| 7,888,110 B2 * | 2/2011 | Deutsch et al. ............ 435/288.5 |
| 8,003,377 B2 * | 8/2011 | Deutsch et al. ............ 435/288.5 |
| 2002/0001856 A1 | 1/2002 | Chow et al. |
| 2002/0052003 A1 | 5/2002 | Alberte et al. |
| 2002/0064885 A1 | 5/2002 | Bedingham et al. |
| 2002/0106715 A1 | 8/2002 | Huberman et al. |
| 2002/0127604 A1 | 9/2002 | Allbritton et al. |
| 2002/0150909 A1 | 10/2002 | Stuelpnagel et al. |
| 2002/0173033 A1 | 11/2002 | Hammerick et al. |
| 2002/0182627 A1 | 12/2002 | Wang et al. |
| 2002/0187074 A1 | 12/2002 | O'Connor et al. |
| 2002/0189374 A1 | 12/2002 | DeSilets et al. |
| 2003/0017079 A1 | 1/2003 | Hahn et al. |
| 2003/0030184 A1 * | 2/2003 | Kim et al. .................... 264/325 |
| 2003/0032048 A1 | 2/2003 | Kim et al. |
| 2003/0032204 A1 | 2/2003 | Walt et al. |
| 2003/0036188 A1 | 2/2003 | Kim et al. |
| 2003/0059764 A1 | 3/2003 | Ravkin et al. |
| 2003/0082632 A1 | 5/2003 | Shumate |
| 2003/0082818 A1 | 5/2003 | Bahnson et al. |
| 2003/0087292 A1 | 5/2003 | Chen et al. |
| 2003/0104494 A1 | 6/2003 | Ravkin et al. |
| 2003/0113833 A1 | 6/2003 | Oka et al. |
| 2003/0124716 A1 | 7/2003 | Hess et al. |
| 2003/0162284 A1 | 8/2003 | Dordick et al. |
| 2003/0189850 A1 | 10/2003 | Sasaki et al. |
| 2003/0211458 A1 | 11/2003 | Sunray et al. |
| 2004/0053354 A1 | 3/2004 | Ikawa et al. |
| 2004/0091397 A1 | 5/2004 | Picard |
| 2004/0118757 A1 | 6/2004 | Terstappen et al. |
| 2004/0216835 A1 | 11/2004 | Tanner et al. |
| 2004/0235143 A1 | 11/2004 | Sasaki et al. |
| 2004/0241783 A1 | 12/2004 | Papkovsky et al. |
| 2004/0262210 A1 | 12/2004 | Westervelt et al. |
| 2005/0014201 A1 | 1/2005 | Deutsch |
| 2005/0026299 A1 | 2/2005 | Bhattacharjee et al. |
| 2005/0064524 A1 | 3/2005 | Deutsch et al. |
| 2005/0074869 A1 | 4/2005 | Yoshida et al. |
| 2005/0089993 A1 | 4/2005 | Boccazzi et al. |
| 2005/0105077 A1 | 5/2005 | Padmanabhan et al. |
| 2005/0106714 A1 | 5/2005 | Zarur et al. |
| 2005/0158845 A1 | 7/2005 | Wikswo et al. |
| 2005/0170498 A1 | 8/2005 | Dolley et al. |
| 2005/0230272 A1 | 10/2005 | Lee et al. |
| 2005/0277125 A1 | 12/2005 | Benn et al. |
| 2006/0041384 A1 | 2/2006 | Kermani et al. |
| 2006/0057557 A1 | 3/2006 | Deutsch et al. |
| 2006/0154233 A1 | 7/2006 | Deutsch |
| 2006/0240548 A1 | 10/2006 | Deutsch et al. |
| 2007/0105089 A1 | 5/2007 | Deutsch |
| 2007/0141555 A1 | 6/2007 | Deutsch |
| 2007/0154357 A1 | 7/2007 | Szlosek |

(56) References Cited

U.S. PATENT DOCUMENTS

| | | | |
|---|---|---|---|
| 2007/0178607 | A1 | 8/2007 | Prober et al. |
| 2007/0292312 | A1 | 12/2007 | Bachman et al. |
| 2007/0292837 | A1 | 12/2007 | Deutsch et al. |
| 2008/0003142 | A1 | 1/2008 | Link et al. |
| 2008/0009051 | A1 | 1/2008 | Deutsch et al. |
| 2008/0063251 | A1 | 3/2008 | Deutsch |
| 2008/0063572 | A1 | 3/2008 | Deutsch et al. |
| 2008/0241874 | A1 | 10/2008 | Deutsch |
| 2009/0105095 | A1 | 4/2009 | Deutsch |
| 2009/0111141 | A1 | 4/2009 | Deutsch |
| 2011/0014688 | A1 | 1/2011 | Deutsch et al. |
| 2013/0071914 | A1 | 3/2013 | Deutsch |

FOREIGN PATENT DOCUMENTS

| | | |
|---|---|---|
| EP | 0094193 | 11/1983 |
| EP | 0602416 | 6/1994 |
| EP | 1262764 | 12/2002 |
| EP | 1566635 | 8/2005 |
| EP | 1691196 | 8/2006 |
| FR | 2890975 | 3/2007 |
| JP | 62-171687 | 7/1987 |
| JP | 06-221988 | 8/1994 |
| JP | 06-237753 | 8/1994 |
| JP | 10-276763 | 10/1998 |
| JP | 11-507724 | 7/1999 |
| JP | 2005-102628 | 4/2005 |
| WO | WO 96/31548 | 10/1996 |
| WO | WO 96/41153 | 12/1996 |
| WO | WO 98/15356 | 4/1998 |
| WO | WO 98/35223 | 8/1998 |
| WO | WO 99/45357 | 9/1999 |
| WO | WO 99/47922 | 9/1999 |
| WO | WO 99/66329 | 12/1999 |
| WO | WO 00/20554 | 4/2000 |
| WO | WO 01/02539 | 1/2001 |
| WO | WO 01/35071 | 5/2001 |
| WO | WO 01/49824 | 7/2001 |
| WO | WO 01/88176 | 11/2001 |
| WO | WO 01/88185 | 11/2001 |
| WO | WO 02/08748 | 1/2002 |
| WO | WO 02/26114 | 4/2002 |
| WO | WO 02/48676 | 6/2002 |
| WO | WO 02/055653 | 7/2002 |
| WO | WO 02/058847 | 8/2002 |
| WO | WO 02/063034 | 8/2002 |
| WO | WO 02/064728 | 8/2002 |
| WO | WO 02/081662 | 10/2002 |
| WO | WO 02/097398 | 12/2002 |
| WO | WO 03/002750 | 1/2003 |
| WO | WO 03/011451 | 2/2003 |
| WO | WO 03/020871 | 3/2003 |
| WO | WO 03/035824 | 5/2003 |
| WO | WO 03/046508 | 6/2003 |
| WO | WO 03/052375 | 6/2003 |
| WO | WO 03/056330 | 7/2003 |
| WO | WO 03/056345 | 7/2003 |
| WO | WO 2004/077009 | 9/2004 |
| WO | WO 2004/113492 | 12/2004 |
| WO | WO 2005/007796 | 1/2005 |
| WO | WO 2005/069001 | 7/2005 |
| WO | WO 2005/103691 | 11/2005 |
| WO | WO 2006/003664 | 1/2006 |
| WO | WO 2006/021959 | 3/2006 |
| WO | WO 2006/043267 | 4/2006 |
| WO | WO 2006/080000 | 8/2006 |
| WO | WO 2007/052245 | 5/2007 |
| WO | WO 2007/074449 | 7/2007 |
| WO | WO 2009/063462 | 5/2009 |
| WO | WO 2009/081409 | 7/2009 |

OTHER PUBLICATIONS

Notice of Allowance Dated Jun. 15, 2010 From the US Patent and Trademark Office Re. U.S. Appl. No. 11/940,996.
Translation of Notice of Reason for Rejection Dated Jul. 23, 2010 From the Japanese Patent Office Re.: Application No. 2006-502647.
Communication Pursuant to Rules 70(2) and 70a(2) EPC Dated Aug. 20, 2012 From the European Patent Office Re. Application No. 08848869.7.
Office Action Dated Aug. 12, 2012 From the Israeli Patent Office Re.: Application No. 172724 and Its Translation Into English.
Supplementary European Search Report and the European Search Opinion Dated Aug. 1, 2012 From the European Patent Office Re. Application No. 08848869.7.
Response Dated Aug. 30, 2010 to Official Action of Jul. 13, 2009 From the US Patent and Trademark Office Re.: U.S. Appl. No. 11/660,783.
Response Dated Aug. 30, 2010 to Official Action of Feb. 23, 2010 From the US Patent and Trademark Office Re.: U.S. Appl. No. 12/084,462.
Official Action Dated Sep. 2, 2010 From the US Patent and Trademark Office Re. U.S. Appl. No. 10/565,240.
Response Dated Sep. 6, 2011 to Notice of Non-Compliant Amendment of Aug. 24, 2011 From the US Patent and Trademark Office Re. U.S. Appl. No. 10/565,240.
Official Action Dated Aug. 31, 2011 From the US Patent and Trademark Office Re.: U.S. Appl. No. 11/660,783.
Response Dated Sep. 19, 2011 to Notice of Non-Compliant Amendment of Aug. 18, 2011 From the US Patent and Trademark Office Re.: U.S. Appl. No. 12/084,462.
Official Action Dated Sep. 10, 2010 From the US Patent and Trademark Office Re.: U.S. Appl. No. 11/646,317.
Official Action Dated Sep. 22, 2011 From the US Patent and Trademark Office Re.: U.S. Appl. No. 11/646,294.
Communication Pursuant to Rules 161(1) and 162 EPC Dated Aug. 25, 2010 From the European Patent Office Re. Application No. 08865081.7.
Official Action Dated Sep. 14, 2010 From the US Patent and Trademark Office Re.: U.S. Appl. No. 11/631,737.
Response Dated Sep. 21, 2010 to Communication Pursuant to Rules 161(1) and 162 EPC of Aug. 25, 2010 From the European Patent Office Re. Application No. 08865081.7.
Communication Pursuant to Rule 58 EPC or Rule 159 EPC Dated Nov. 24, 2010 From the European Patent Office Re. Application No. 10183774.8.
Response Dated Jan. 3, 2011 to Communication Pursuant to Rule 58 EPC or Rule 159 EPC of Nov. 24, 2010 From the European Patent Office Re. Application No. 10183774.8.
Response Dated Jan. 12, 2011 to Office Action of Oct. 5, 2010 From the Israel Patent Office Re. Application No. 184818.
Official Action Dated Feb. 1, 2011 From the US Patent and Trademark Office Re.: U.S. Appl. No. 11/631,737.
Office Action Dated Feb. 2, 2012 From the Israel Patent Office Re.: Application No. 173170 and Its Translation Into English.
Official Action Dated Mar. 1, 2012 From the US Patent and Trademark Office Re.: U.S. Appl. No. 12/084,462.
Interview Summary Dated Feb. 11, 2011 From the US Patent and Trademark Office Re.: U.S. Appl. No. 11/883,028.
Response Dated Jan. 20, 2011 to Official Action of Oct. 27, 2010 From the US Patent and Trademark Office Re.: U.S. Appl. No. 12/890,668.
Official Action Dated Mar. 6, 2012 From the US Patent and Trademark Office Re. U.S. Appl. No. 12/155,643.
Response Dated Feb. 7, 2011 to Communication Pursuant to Article 94(3) EPC of Aug. 6, 2010 From the European Patent Office Re.: Application No. 04714873.9.
Official Action Dated Sep. 29, 2010 From the US Patent and Trademark Office Re.: U.S. Appl. No. 11/883,028.
Partial European Search Report Dated Oct. 27, 2011 From the European Patent Office Re. Application No. 11170000.1.
Communication Pursuant to Article 94(3) EPC Dated Nov. 16, 2011 From the European Patent Office Re. Application No. 04744911.1.
Response Dated Nov. 1, 2011 to Official Action of Oct. 19, 2011 From the US Patent and Trademark Office Re. U.S. Appl. No. 12/155,643.
Response Dated Nov. 30, 2011 to Office Action of Jul. 1, 2010 From the Israeli Patent Office Re.: Application No. 172724.

(56) References Cited

OTHER PUBLICATIONS

Response Dated Oct. 31, 2011 to Official Action of Jul. 21, 2011 From the US Patent and Trademark Office Re. U.S. Appl. No. 12/712,232.
Office Action Dated Feb. 28, 2011 From the Israel Patent Office Re. Application No. 180568 and Its Translation Into English.
Official Action Dated Mar. 9, 2011 From the US Patent and Trademark Office Re.: U.S. Appl. No. 11/660,783.
Response Dated Mar. 22, 2011 to Official Action of Dec. 22, 2010 From the US Patent and Trademark Office Re.: U.S. Appl. No. 11/883,028.
Official Action Dated Mar. 16, 2011 From the US Patent and Trademark Office Re. U.S. Appl. No. 10/561,839.
Cornell University "All About Birds: Optical Quality", Cornell University, 2 P., Oct. 3, 2010.
Invitation Pursuant to Article 94(3) and Rule 71(1) EPC Dated Apr. 8, 2011 From the European Patent Office Re. Application No. 01982673.4.
Notice of Allowance Dated Mar. 31, 2011 From the US Patent and Trademark Office Re.: U.S. Appl. No. 12/890,668.
Official Action Dated Mar. 31, 2011 From the US Patent and Trademark Office Re.: U.S. Appl. No. 10/492,531.
Seahorse Bioscience "Designed for Scientists by Scienctists. How the XF24 Extracellular Flux Analyzer Works", Product Description, Seahorse Bioscience, 4 P., 2008.
Seahorse Bioscience "XF24 Extracellular Flux Analyzer", Product Description, Seahorse Bioscience, 3 P., 2008.
Communication Pursuant to Article 94(3) EPC Dated Apr. 11, 2012 From the European Patent Office Re. Application No. 10183774.8.
Invitation Pursuant to Rule 63(1) EPC Dated May 3, 2011 From the European Patent Office Re. Application No. 10183774.8.
Official Action Dated Apr. 15, 2011 From the US Patent and Trademark Office Re.: U.S. Appl. No. 12/084,462.
Official Action Dated Apr. 22, 2011 From the US Patent and Trademark Office Re.: U.S. Appl. No. 11/646,294.
Restriction Official Action Dated Dec. 12, 2011 From the US Patent and Trademark Office Re. U.S. Appl. No. 13/184,631.
Response Dated Dec. 21, 2011 to Communication Pursuant to Article 94(3) EPC of Aug. 29, 2011 From the European Patent Office Re. Application No. 04745001.0.
Official Action Dated Dec. 19, 2011 From the US Patent and Trademark Office Re.: U.S. Appl. No. 10/492,531.
Official Action Dated Dec. 23, 2011 From the US Patent and Trademark Office Re. U.S. Appl. No. 10/565,240.
Official Action Dated Nov. 1, 2010 From the US Patent and Trademark Office Re.: U.S. Appl. No. 11/883,028.
Official Action Dated Dec. 9, 2010 From the US Patent and Trademark Office Re. U.S. Appl. No. 10/565,240.
Official Action Dated Dec. 22, 2010 From the US Patent and Trademark Office Re.: U.S. Appl. No. 11/883,028.
Proceeding Further With the European Patent Application Pursuant to Rule 70(2) EPC Dated Nov. 10, 2009 From the European Patent Office Re. Application No. 04745001.0.
Response Dated Jan. 20, 2011 to Proceeding Further With the European Patent Application Pursuant to Rule 70(2) EPC of Nov. 10, 2009 From the European Patent Office Re. Application No. 04745001.0.
Response Dated Nov. 8, 2010 to Official Action of Sep. 10, 2010 From the US Patent and Trademark Office Re.: U.S. Appl. No. 11/646,317.
Response Dated Nov. 15, 2010 to Official Action Dated Sep. 14, 2010 From the US Patent and Trademark Office Re.: U.S. Appl. No. 11/631,737.
Response Dated Nov. 15, 2010 to Official Action of Nov. 1, 2010 From the US Patent and Trademark Office Re.: U.S. Appl. No. 11/883,028.
Response Dated Dec. 16, 2010 to Official Action of Aug. 17, 2010 From the US Patent and Trademark Office Re.: U.S. Appl. No. 10/561,839.
Response Dated Dec. 20, 2010 to Official Action of Sep. 23, 2010 From the US Patent and Trademark Office Re.: U.S. Appl. No. 10/492,531.
Response Dated Nov. 30, 2010 to Communication Pursuant to Article 94(3) EPC of Aug. 5, 2010 From the European Patent Office Re. Application No. 05757567.2.
Communication Pursuant to Article 94(3) EPC Dated May 22, 2012 From the European Patent Office Re.: Application No. 04714873.9.
Communication Pursuant to Article 94(3) EPC Dated Jun. 25, 2012 From the European Patent Office Re. Application No. 04744911.1.
Official Action Dated Jun. 22, 2012 From the US Patent and Trademark Office Re. U.S. Appl. No. 13/019,320.
Lee et al. "An Equibiaxial Strain System for Cultured Cells", The American Journal of Physiology, XP008152868, 271(4): C1400-C1408, Oct. 1996.
Tschumperlin et al. "Equibiaxial Deformation-Induced Injury of Alveolar Epithelial Cells In Vitro", American Journal of Physiology, 275(6/Pt.1): L1173-L1183, Jan. 1, 1998.
Response Dated Jun. 9, 2011 to Official Action of Dec. 9, 2010 From the US Patent and Trademark Office Re. U.S. Appl. No. 10/565,240.
Response Dated Jun. 29, 2011 to Official Action of Mar. 31, 2011 From the US Patent and Trademark Office Re.: U.S. Appl. No. 10/492,531.
Response Dated Jul. 12, 2011 to Official Action of Mar. 16, 2011 From the US Patent and Trademark Office Re. U.S. Appl. No. 10/561,839.
Response Dated Jun. 28, 2011 to Invitation Pursuant to Rule 63(1) EPC of May 3, 2011 From the European Patent Office Re. Application No. 10183774.8.
Official Action Dated Jul. 30, 2012 From the US Patent and Trademark Office Re. U.S. Appl. No. 12/155,643.
Official Action Dated Aug. 2, 2012 From the US Patent and Trademark Office Re. U.S. Appl. No. 12/712,232.
Communication Pursuant to Article 94(3) EPC Dated Aug. 6, 2010 From the European Patent Office Re.: Application No. 04714873.9.
Office Action Dated Jul. 1, 2010 From the Israeli Patent Office Re.: Application No. 172724 and Its Translation Into English.
Official Action Dated Aug. 17, 2010 From the US Patent and Trademark Office Re.: U.S. Appl. No. 10/561,839.
Notice of Non-Compliant Amendment Dated Aug. 18, 2011 From the US Patent and Trademark Office Re.: U.S. Appl. No. 12/084,462.
Notice of Non-Compliant Amendment Dated Aug. 24, 2011 From the US Patent and Trademark Office Re. U.S. Appl. No. 10/565,240.
Reponse Dated Aug. 4, 2011 to Official Action of Apr. 15, 2011 From the US Patent and Trademark Office Re.: U.S. Appl. No. 12/084,462.
Response Dated Aug. 4, 2011 to Official Action of May 23, 2011 From the US Patent and Trademark Office Re.: U.S. Appl. No. 11/646,317.
Response Dated Aug. 17, 2011 to Office Action of Apr. 12, 2011 From the Israel Patent Office Re.: Application No. 173170.
Response Dated Aug. 22, 2011 to Official Action of Apr. 22, 2011 From the US Patent and Trademark Office Re.: U.S. Appl. No. 11/646,294.
European Search Report and the European Search Opinion Dated Mar. 13, 2012 From the European Patent Office Re. Application No. 11170000.1.
Communication Pursuant to Article 94(3) EPC Dated Aug. 9, 2010 From the European Patent Office Re. Application No. 01982673.4.
Official Action Dated Jul. 21, 2011 From the US Patent and Trademark Office Re. U.S. Appl. No. 12/712,232.
Office Action Dated Oct. 5, 2010 From the Israel Patent Office Re. Application No. 184818 and Its Translation Into English.
Response Dated Oct. 4, 2010 to Official Action of Sep. 2, 2010 From the US Patent and Trademark Office Re. U.S. Appl. No. 10/565,240.
Response Dated Feb. 23, 2011 to Official Action of Jan. 19, 2011 From the US Patent and Trademark Office Re.: U.S. Appl. No. 11/646,317.
Communication Pursuant to Rules 70(2) and 70a(2) EPC and Reference to Rule 39(1) EPC Dated Apr. 16, 2012 From the European Patent Office Re. Application No. 11170000.1.
Notification of European Publication Number and Information on the Applicaiton of Article 67(3) EPC Dated May 18, 2011 From the European Patent Office Re. Application No. 10183774.8.

(56) References Cited

OTHER PUBLICATIONS

Official Action Dated May 23, 2011 From the US Patent and Trademark Office Re.: U.S. Appl. No. 11/646,317.
Official Action Dated Feb. 5, 2007 From the US Patent and Trademark Office Re.: U.S. Appl. No. 10/916,380.
Official Action Dated Feb. 19, 2008 From the US Patent and Trademark Office Re.: U.S. Appl. No. 10/492,531.
Official Action Dated Sep. 20, 2007 From the US Patent and Trademark Office Re.: U.S. Appl. No. 10/492,531.
Official Action Dated Jan. 25, 2007 From the US Patent and Trademark Office Re.: U.S. Appl. No. 10/492,531.
Communication Pursuant to Article 94(3) EPC Dated Feb. 13, 2009 From the European Patent Office Re.: Application No. 05763452.9.
Communication Pursuant to Article 94(3) EPC Dated Jun. 16, 2009 From the European Patent Office Re.: Application No. 04714873.9.
Communication Pursuant to Article 94(3) EPC Dated Feb. 29, 2008 From the European Patent Office Re.: 05763452.9.
Communication Relating to the Results of the Partial International Search Dated May 20, 2009 From the International Searching Authority Re.: Application No. PCT/IL2008/001678.
International Preliminary Report on Patentability Dated Feb. 20, 2006 From the International Bureau of WIPO Re.: Application No. PCT/IL2004/000661.
International Preliminary Report on Patentability Dated May 30, 2007 From the International Bureau of WIPO Re.: Application No. PCT/IL2005/001078.
International Preliminary Report on Patentability Dated Mar. 8, 2007 From the International Bureau of WIPO Re.: Application No. PCT/IL2005/000914.
International Preliminary Report on Patentability Dated Aug. 9, 2007 From the International Bureau of WIPO Re.: Application No. PCT/IL2005/000801.
International Preliminary Report on Patentability Dated Jul. 10, 2008 From the International Bureau of WIPO Re.: Application No. PCT/IL2006/001487.
International Preliminary Report on Patentability Dated Jan. 18, 2007 From the International Bureau of WIPO Re.: Application No. PCT/IL2005/000719.
International Preliminary Report on Patentability Dated Nov. 28, 2007 From the International Bureau of WIPO Re.: Application No. PCT/IL2006/000483.
International Search Report Dated Mar. 2, 2005 From the International Searching Authority Re.: Application No. PCT/IL04/00661.
International Search Report Dated Feb. 7, 2006 From the International Searching Authority Re.: Application No. PCT/IL2005/001078.
International Search Report Dated Nov. 7, 2005 From the International Searching Authority Re.: PCT/IL2005/000801.
International Search Report Dated Nov. 9, 2004 From the International Searching Authority Re.: Application No. PCT/IL04/00571.
International Search Report Dated Sep. 10, 2009 From the International Searching Authority Re.: Application No. PCT/IL2008/001678.
International Search Report Dated Sep. 11, 2006 From the International Seaching Authority Re.: Application No. PCT/IL2006/000483.
International Search Report Dated May 13, 2009 From the International Searching Authority Re.: Application No. PCT/IL08/01492.
International Search Report Dated Nov. 15, 2005 From the International Searching Authority Re.: PCT/IL2005/000719.
International Search Report Dated Feb. 16, 2005 From the International Searching Authority Re.: PCT/IL04/00194.
International Search Report Dated Jan. 17, 2003 From the International Searching Authority Re.: Application No. PCT/IL01/00992.
International Search Report Dated Feb. 21, 2006 From the international Searching Authority Re.: Application No. PCT/IL2005/000914.
International Search Report Dated Sep. 21, 2007 From the International Searching Authority Re.: PCT/IL2006/001487.
International Search Report Dated Dec. 27, 2001 From the International Searching Authority Re.: Application No. PCT/IL01/00443.
Invitation to Pay Additional Fees Dated Mar. 3, 2009 From the International Searching Authority Re.: Application No. PCT/IL08/01492.
Notice of Allowance Dated Mar. 4, 2008 From the US Patent and Trademark Office Re.: U.S. Appl. No. 10/546,784.
Notice of Allowance Dated Jan. 7, 2008 From the US Patent and Trademark Office Re.: U.S. Appl. No. 10/938,951.
Office Action Dated Mar. 8, 2006 From the Israeli Patent Office Re.: Application No. 138314.
Office Action Dated Apr. 12, 2007 From the Israeli Patent Office Re.: Application No. 138314.
Office Action Dated Jul. 14, 2009 From the Israeli Patent Office Re.: Application No. 172724 and Its Translation Into English.
Office Action Dated May 15, 2008 From the Israeli Patent Office Re.: U.S. Appl. No. 10/916,380.
Office Action Dated Jul. 19, 2006 From the Israeli Patent Office Re.: Application No. 138314.
Office Action Dated Mar. 22, 2009 From the Israeli Patent Office Re.: Application No. 170492 and Its Translation Into English.
Office Action Dated Sep. 29, 2003 From the Israeli Patent Office Re.: Application No. 136232.
Official Action Dated Mar. 5, 2010 From the US Patent and Trademark Office Re.: U.S. Appl. No. 10/561,839.
Official Action Dated Jul. 13, 2009 From the US Patent and Trademark Office Re.: U.S. Appl. No. 11/660,783.
Official Action Dated Dec. 14, 2007 From the US Patent and Trademark Office Re.: U.S. Appl. No. 10/916,380.
Official Action Dated Nov. 14, 2008 From the US Patent and Trademark Office Re.: U.S. Appl. No. 10/492,531.
Official Action Dated Oct. 16, 2006 From the US Patent and Trademark Office Re.: U.S. Appl. No. 10/492,531.
Official Action Dated Dec. 18, 2006 From the US Patent and Trademark Office Re.: U.S. Appl. No. 10/276,080.
Official Action Dated Oct. 22, 2007 From the US Patent and Trademark Office Re.: U.S. Appl. No. 11/492,531.
Official Action Dated Feb. 23, 2010 From the US Patent and Trademark Office Re.: U.S. Appl. No. 12/084,462.
Official Action Dated Mar. 23, 2005 From the US Patent and Trademark Office Re.: U.S. Appl. No. 10/276,080.
Official Action Dated Aug. 25, 2006 From the US Patent and Trademark Office Re.: U.S. Appl. No. 10/276,080.
Official Action Dated Aug. 28, 2007 From the US Patent and Trademark Office Re.: U.S. Appl. No. 10/916,380.
Official Action Dated Jan. 28, 2010 From the US Patent and Trademark Office Re.: U.S. Appl. No. 10/492,531.
Official Action Dated Jun. 29, 2009 From the US Patent and Trademark Office Re.: U.S. Appl. No. 10/492,531.
Response Dated Dec. 14, 2009 to Office Action of Jul. 14, 2009 From the Israel Patent Office Re.: Application No. 172724.
Response Dated Apr. 29, 2005 to Communication Pursuant to Article 96(2) EPC of Dec. 23, 2004 From the European Patent Office Re.: Application No. 01934272.4.
Response Dated Dec. 29, 2009 to Office Action of Sep. 2, 2009 From the Israel Patent Office Re.: Application No. 200559.
Supplementary European Search Report Dated Feb. 20, 2006 From the European Patent Office Re.: Application No. 04714873.9.
Supplementary European Search Report Dated Oct. 22, 2009 From the European Patent Office Re.: Application No. 04744911.1.
Supplementary European Search Report Dated Oct. 22, 2009 From the European Patent Office Re.: Application No. 04745001.0.
Supplementary European Search Report Dated Oct. 26, 2004 From the European Patent Office Re.: Application No. EP 01934272.
Translation of Notice of Reason for Rejection Dated Nov. 27, 2007 From Japanes Patent Office Re.: Application No. 2003-538325.
Translation of Notice of Reason for Rejection Dated Mar. 30, 2010 From the Japanese Patent Office Re.: Application No. 2006-502647.
Written Opinion Dated Sep. 10, 2009 From the International Searching Authority Re.: Application No. PCT/IL2008/001678.
Written Opinion Dated May 13, 2009 From the International Searching Authority Re.: Application No. PCT/IL08/01492.

(56) References Cited

OTHER PUBLICATIONS

Written Opinion Dated Nov. 15, 2005 From the International Searching Authority Re.: Application No. PCT/IL2005/000719.
Aplin et al. "Protein-Derivatised Glass Coverslips for the Study of Cell-to-Substratum Adhesion", Analytical Biochemistry, 113: 144-148, 1981.
Arikawa et al. "Microbial Biosensors Based on Respiratory Inhibition", Methos in Biotechnology, 6(Chap.16): 225-235, 1998.
Baruch et al. "Enzyme Activity—It's All About Image", Trends in Cell Biology, 14(1): 29-35, 2004.
Bedner et al. "Enzyme Kinetic Reactions and Fluorochrome Uptake Rates Measured in Individual Cells by Laser Scanning Cytometry", Cytometry, 33(1): 1-9, 1998. Abstract, p. 2, col. 1, §4—col. 2, §1, p. 8, col. 2, §2.
Burlage et al. "Living Biosensors for the Management and Manipulation of Microbial Consortia", Annual Reviews in Microbiology, 48: 291-309, 1994.
Craighead et al. "Textured Surfaces: Optical Storage and Other Applications", Journal of Vacuum Science and Technology 20 (3): 316, 1982. Abstract.
Darzynkiewicz et al. "Laser-Scanning Cytometry: A New Instrumentation With Many Applications", Experimental Cell Research, 249(1): 1-12, 1999. Abstract, p. 2, col. 2, §4—p. 4, col. 2, §2, p. 8, col. 1, §1—col. 2, §2.
Deutsch et al. "Apparatus for High-Precision Repetitive Sequential Optical Measurement of Living Cells", Cytometry, 16: 214-226, 1994.
Deutsch et al. "Microplate Cell-Retaining Methodology for High-Content Analysis of Individual Non-Adherent Unanchored Cells in a Population", Biomedical Microdevices, 8: 361-374, 2006.
Dive et al. "Improved Methodology for Intracellular Enzyme Reaction and Inhibition Kinetics by Flow Cytometry", Cytometry Journal of Society for Analytical Cytology, 8(6): 552-561, 1987.
Dolbeare "Fluorescent Staining of Enzymes for Flow Cytometry", Methods in Cell Biology, 33(Chap.8): 81-88, 1990.
Ducrée "Polymer Prototyping von mikrofluidischen Strukturen. Projekt", Insitut für Mikrosystemtechnik, Albert-Ludwigs-Universität Freiburg i. Br., IMTEK, 4 P., 2004. Retrieved From the Internet: http://images.google.com/imgres?imgurl=http://www.imtek.de/anwendungen/content/upload/vorlesung/133/133-03-14_prototyping_hydrophobic.jpg&imgrefurl=http://www.imtek.de/content/projekte.php%3FIs%3D3%26nr%3D133&h=299&w=429&.
Eisenthal et al. "Infection of K562 Cells With Influenza A Virus Increases Their Susceptibility to Natural Killer Lysis", Pathobiology, 65: 331-340, 1997.
Hansen et al. "Quantification of Bioavailable Chlortetracycline in Pig Feces Using a Bacterial Whole-Cell Biosensor", Veterinary Microbiology, 87: 51-57, 2002.
Kiguchi et al. "Induction of Urokinase-Type Plasminogen Activator by the Anthracycline Antibiotic in Human RC-K8 Lymphoma and H69 Lung-Carcinoma Cells", International Journal of Cancer, 93: 792-797, 2001.
Klingel et al. "Flow Cytometric Determination of Serine Proteinase Activities in Living Cells With Rhodamine 110 Substrates", Methods in Cell Biology, 41(Chap.29): 449-460, 1994.
Koh et al. "Poly(Ethylene Glycol) Hydrogel Microstructures Encapsulating Living Cells", Langmuir, 18(7): 2459-2462, 2002. p. 2459-2462, Fig.3.
Kovacic et al. "Mechanisms of Carcinogenesis: Focus on Oxidative Stress and Electron Transfer", Current Medicinal Chemistry, 8: 773-796, 2001.
Lansing Taylor et al. "Real-Time Molecular and Cellular Analysis: The New Frontier of Drug Discovery", Current Opinion in Biotechnology, 12: 75-81, 2001.
Malin-Berdel et al. "Flow Cytometric Determination of Esterase and Phosphatase Activities and Kinetics in Hematopoietic Cells With Fluorogenic Substrates", Cytometry, 1(3): 222-228, 1980.
Mrksich et al. "Using Self-Assembled Monolayers to Understand the Interactions of Man-Made Surfaces With Proteins and Cells", Annual Reviews in Biophysics and Biomolecular Structure, 25: 55-78, 1996.
Nooter et al. "On-Line Flow Cytometry. A Versatile Method for Kinetic Measurement", Methods in Cell Biology, 41(Chap.32): 509-526, 1994.
Riedel et al. "Arxula Adeninivorans Based Sensor for the Estimation of Bod", Analytical Letters, 31(1): 1-12, 1998.
Schroeder et al. "Coordination of Cell Growth in Cocultures by a Genetic Proliferation Control System", Biotechnology and Bioengineering, 78(3): 346-352, 2002.
Simonian et al. "Microbial Biosensors Based on Potentiometric Detection", Methods in Biotechnology, 6(Chap.17): 237-248, 1998.
Singhvi et al. "Engineering Cell Shape and Function", Science, 264: 696-698, 1994.
Stevens et al. "Quorum Sensing in Vibrio Fischeri: Essential Elements for Activation of the Luminescence Genes", Journal of Bacteriology, 179(2): 557-562, Jan. 1997.
Suehiro et al. "The Dielectrophoretic Movement and Positioning of a Biological Cell Using a Three-Dimensional Grid Electrode System", J. Phys. D. Appl. Phys, vol. 31 p. 3298-3305, 1998.
Sunray et al. "Cell Activation Influences Cell Staining Kinetics", Spectrochimica Part A, 53: 1645-1653, 1997.
Sunray et al. "Determination of Individual Cell Michaelis-Menten Constants", Cytometry, 47(1): 8-16, 2002.
Sunray et al. "Determination of the Michaelis-Menten Constant (Km) of Intracellular Enzymatic Reaction for Individual Live Lymphocytes", Cytometry Supplement, 10: 68-69, & The XX Congress of the International Society for Analytical Cytology, Montpellier, F, 2000.
Sunray et al. "The Trace and Subgrouping of Lymphocyte Activation by Dynamic Fluorescence Intensity and Polarization Measurements", Biochemical and Biophysical Research Communications, 261(3): 712-719, 1999. Abstract, p. 713, col. 1, §5, col. 2, §7—p. 714, col. 2, §1.
Tixier et al. Catching and Attaching Cells Using an Array of Microholes, 2nd Conference of the Society for Chemistry and Micro Systems, p. 60, 2000. Abstract.
Turek et al. "Leucine Aminopeptidase Activity by Flow Cytometry", Methods in Cell Biology, 41(Chap.30): 461-468, 1994.
Watson et al. "Enzyme Kinetics", Methods in Cell Biology, 41: 469-508, 1994.
Yamamura et al. "Single-Cell Microarray for Analyzing Cellular Response", Analytical Chemistry, 77(24): 8050-8056, 2005.
International Preliminary Report on Patentability Dated May 27, 2010 From the International Bureau of WIPO Re.: Application No. PCT/IL2008/001492.
International Preliminary Report on Patentability Dated May 27, 2010 From the International Preliminary Examining Authority Re.: Application No. PCT/IL2008/001678.
Response Dated May 25, 2010 to Official Action of Jan. 28, 2010 From the US Patent and Trademark Office Re.: U.S. Appl. No. 10/492,531.
Response Dated Jun. 15, 2010 to Notice of Reason for Rejection of Mar. 30, 2010 From the Japanese Patent Office Re. Application No. 2006-502647.
Notice of Allowance Dated Jun. 9, 2011 From the US Patent and Trademark Office Re.: U.S. Appl. No. 11/883,028.
Communication Pursuant to Article 94(3) EPC Dated Jun. 25, 2012 From the European Patent Office Re. Application No. 04745001.0.
Official Action Dated Jun. 21, 2012 From the US Patent and Trademark Office Re.: U.S. Appl. No. 10/492,531.
Response Dated Oct. 10, 2010 to Notice of Reason for Rejection of Jul. 23, 2010 From the Japanese Patent Office Re.: Application No. 2006-502647.
Response Dated Nov. 21, 2011 to Communication Pursuant to Article 94(3) EPC of Aug. 4, 2011 From the European Patent Office Re. Application No. 08865081.7.
Interview Summary Dated Jan. 23, 2012 From the US Patent and Trademark Office Re.: U.S. Appl. No. 12/084,462.
Restriction Official Action Dated Jan. 19, 2012 From the US Patent and Trademark Office Re. U.S. Appl. No. 13/019,320.

(56) References Cited

OTHER PUBLICATIONS

Official Action Dated Jan. 19, 2011 From the US Patent and Trademark Office Re.: U.S. Appl. No. 11/646,317.
Response Dated Jan. 24, 2011 to Official Action of Sep. 23, 2010 From the US Patent and Trademark Office Re.: U.S. Appl. No. 11/646,294.
Response Dated Jun. 1, 2011 to Official Action of Feb. 1, 2011 From the US Patent and Trademark Office Re.: U.S. Appl. No. 11/631,737.
Response Dated Jun. 9, 2011 to Official Action of Mar. 9, 2011 From the US Patent and Trademark Office Re.: U.S. Appl. No. 11/660,783.
Response Dated Jun. 7, 2010 to Official Action of Mar. 5, 2010 From the US Patent and Trademark Office Re.: U.S. Appl. No. 10/561,839.
European Search Report and the European Search Opinion Dated Aug. 1, 2011 From the European Patent Office Re. Application No. 10183774.8.
Office Action Dated Apr. 12, 2011 From the Israel Patent Office Re.: Application No. 173170 and Its Translation Into English.
Gonzalez et al. "Cell-Based Assays and Instrumentation for Screening Ion-Channels Targets", Drug Discovery Today, DDT, XP001026838, 4(9): 431-439, Sep. 1, 1999.
Communication Pursuant to Article 94(3) EPC Dated Aug. 4, 2011 From the European Patent Office Re. Application No. 08865081.7.
Communication Pursuant to Article 94(3) EPC Dated Aug. 29, 2011 From the European Patent Office Re. Application No. 04745001.0.
Communication Pursuant to Article 94(3) EPC Dated Sep. 6, 2012 From the European Patent Office Re. Application No. 10183774.8.
Communication Pursuant to Article 94(3) EPC Dated Sep. 26, 2012 From the European Patent Office Re. Application No. 04714873.9.
Official Action Dated Sep. 23, 2010 From the US Patent and Trademark Office Re.: U.S. Appl. No. 10/492,531.
Official Action Dated Sep. 23, 2010 From the US Patent and Trademark Office Re.: U.S. Appl. No. 11/646,294.
Communication Pursuant to Rules 70(2) and 70a(2) EPC and Reference to Rule 39(1) EPC Dated Sep. 5, 2011 From the European Patent Office Re. Application No. 10183774.8.
Official Action Dated Oct. 18, 2011 From the US Patent and Trademark Office Re. : U.S. Appl. No. 11/631,737.
Official Action Dated Oct. 18, 2011 From the US Patent and Trademark Office Re.: U.S. Appl. No. 12/084,462.
Official Action Dated Oct. 19, 2011 From the US Patent and Trademark Office Re. U.S. Appl. No. 12/155,643.
Communication Pursuant to Article 94(3) EPC Dated Dec. 2, 2011 From the European Patent Office Re.: Application No. 04714873.9.
Official Action Dated Nov. 22, 2011 From the US Patent and Trademark Office Re.: U.S. Appl. No. 11/646,317.
Official Action Dated Nov. 23, 2011 From the US Patent and Trademark Office Re.: U.S. Appl. No. 10/561,839.
Official Action Dated Oct. 27, 2010 From the US Patent and Trademark Office Re.: U.S. Appl. No. 12/890,668.
Official Action Dated Dec. 16, 2012 From the US Patent and Trademark Office Re. U.S. Appl. No. 13/019,320.
Official Action Dated Nov. 14, 2012 From the US Patent and Trademark Office Re. U.S. Appl. No. 13/184,631.
Restriction Official Action Dated Nov. 15, 2012 From the US Patent and Trademark Office Re. U.S. Appl. No. 12/810,868.
Communication Pursuant to Article 94(3) EPC Dated Nov. 23, 2012 From the European Patent Office Re. Application No. 01982673.4.
Applicant-Initiated Interview Summary Dated Dec. 20, 2012 From the US Patent and Trademark Office Re. U.S. Appl. No. 13/184,631.
Office Action Dated Dec. 17, 2012 From the Israel Patent Office Re. Application No. 205769 and Its Translation Into English.
Translation of Office Action Dated Sep. 20, 2012 From the Israel Patent Office Re. Application No. 138314.
Official Action Dated Sep. 28, 2012 From the US Patent and Trademark Office Re. U.S. Appl. No. 10/561,839.
Office Action Dated Dec. 31, 2012 From the Israel Patent Office Re. Application No. 206588 and Its Translation Into English.
Official Action Dated Feb. 13, 2013 From the US Patent and Trademark Office Re. U.S. Appl. No. 12/810,868.
Official Action Dated Mar. 15, 2013 From the US Patent and Trademark Office Re. U.S. Appl. No. 13/019,320.
Official Action Dated Mar. 13, 2013 From the US Patent and Trademark Office Re.: U.S. Appl. No. 10/492,531.
Notice of Allowance Dated Apr. 1, 2013 From the US Patent and Trademark Office Re. U.S. Appl. No. 13/184,631.
Official Action Dated Dec. 18, 2012 From the US Patent and Trademark Office Re. U.S. Appl. No. 13/019,320.
Invitation Pursuant to Article 94(3) and Rule 71(1) EPC Dated Jun. 25, 2013 From the European Patent Office Re. Application No. 04744911.1.
Office Action Dated Apr. 12, 2011 From the Israel Patent Office Re. Application No. 173170 and Its Translation Into English.
Official Action Dated Jun. 20, 2013 From the US Patent and Trademark Office Re. U.S. Appl. No. 12/155,643.
Restriction Official Action Dated Apr. 25, 2013 From the US Patent and Trademark Office Re. U.S. Appl. No. 13/651,522.
Gelest "Optical Materials", 'Gelest', Enabling Your Technology, Downloaded from Internet, 36 P., 2007.
Office Action Dated May 16, 2013 From the Israel Patent Office Re. Application No. 173170 and Its Translation Into English.
Official Action Dated Jul. 15, 2013 From the US Patent and Trademark Office Re. U.S. Appl. No. 12/810,868.
Official Action Dated Jul. 29, 2013 From the US Patent and Trademark Office Re. U.S. Appl. No. 12/712,232.
Advisory Action Before the Filing of an Appeal Brief Dated Aug. 29, 2013 From the US Patent and Trademark Office Re. U.S. Appl. No. 13/019,320.
Applicant-Initiated Interview Summary Dated Aug. 16, 2013 From the US Patent and Trademark Office Re. U.S. Appl. No. 12/810,868.
Communication Pursuant to Article 94(3) EPC Dated Oct. 4, 2013 From the European Patent Office Re. Application No. 04745001.0.
Official Action Dated Sep. 27, 2013 From the US Patent and Trademark Office Re. U.S. Appl. No. 13/651,522.
Official Action Dated Sep. 30, 2013 From the US Patent and Trademark Office Re. U.S. Appl. No. 10/561,839.
Summons to Attend Oral Proceedings Pursuant to Rule 115(1) EPC Dated Aug. 14, 2013 From the European Patent Office Re. Application No. 01982673.4.
Summons to Attend Oral Proceedings Pursuant to Rule 115(1) EPC Dated Aug. 14, 2013 From the European Patent Office Re. Application No. 10183774.8.

\* cited by examiner

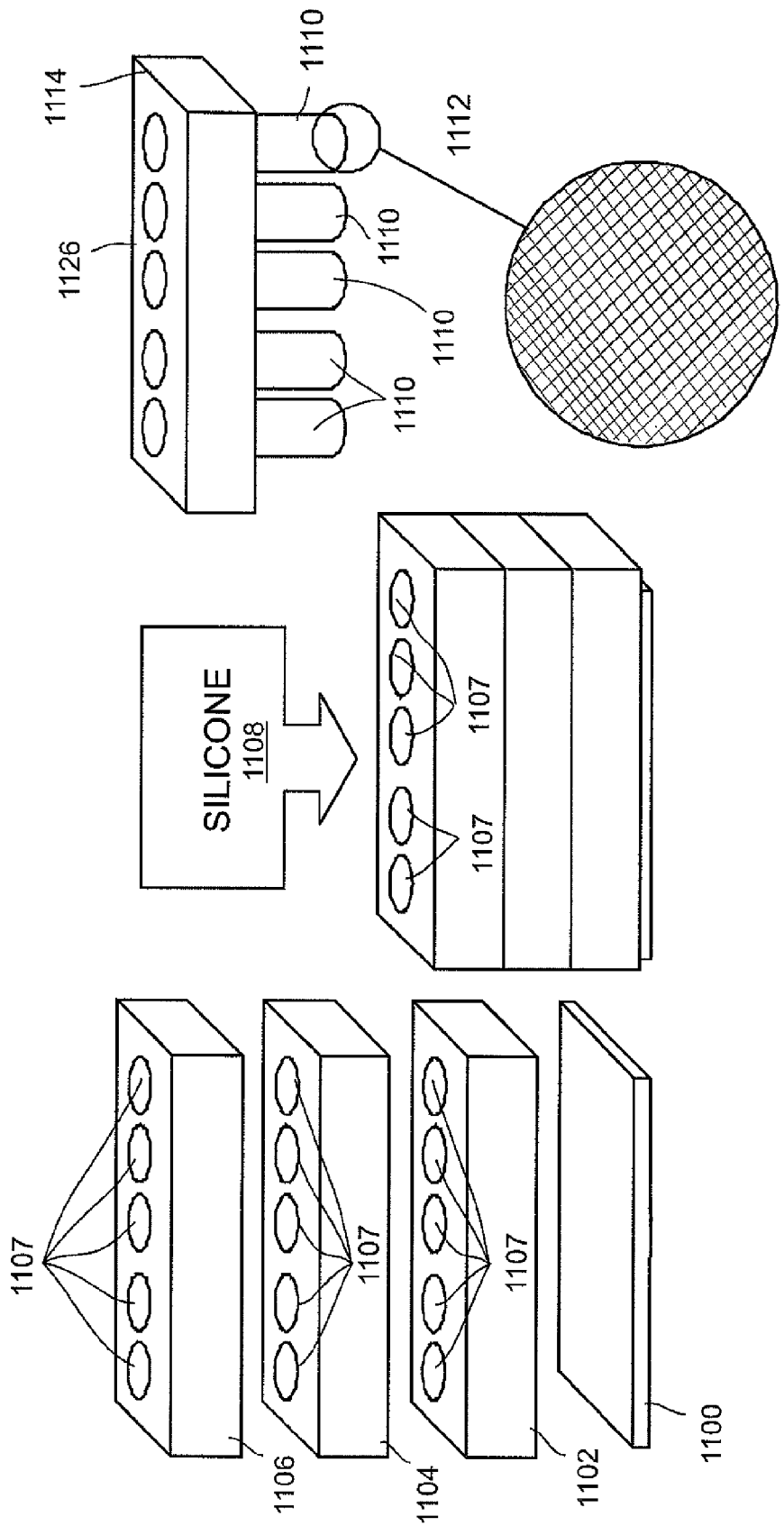

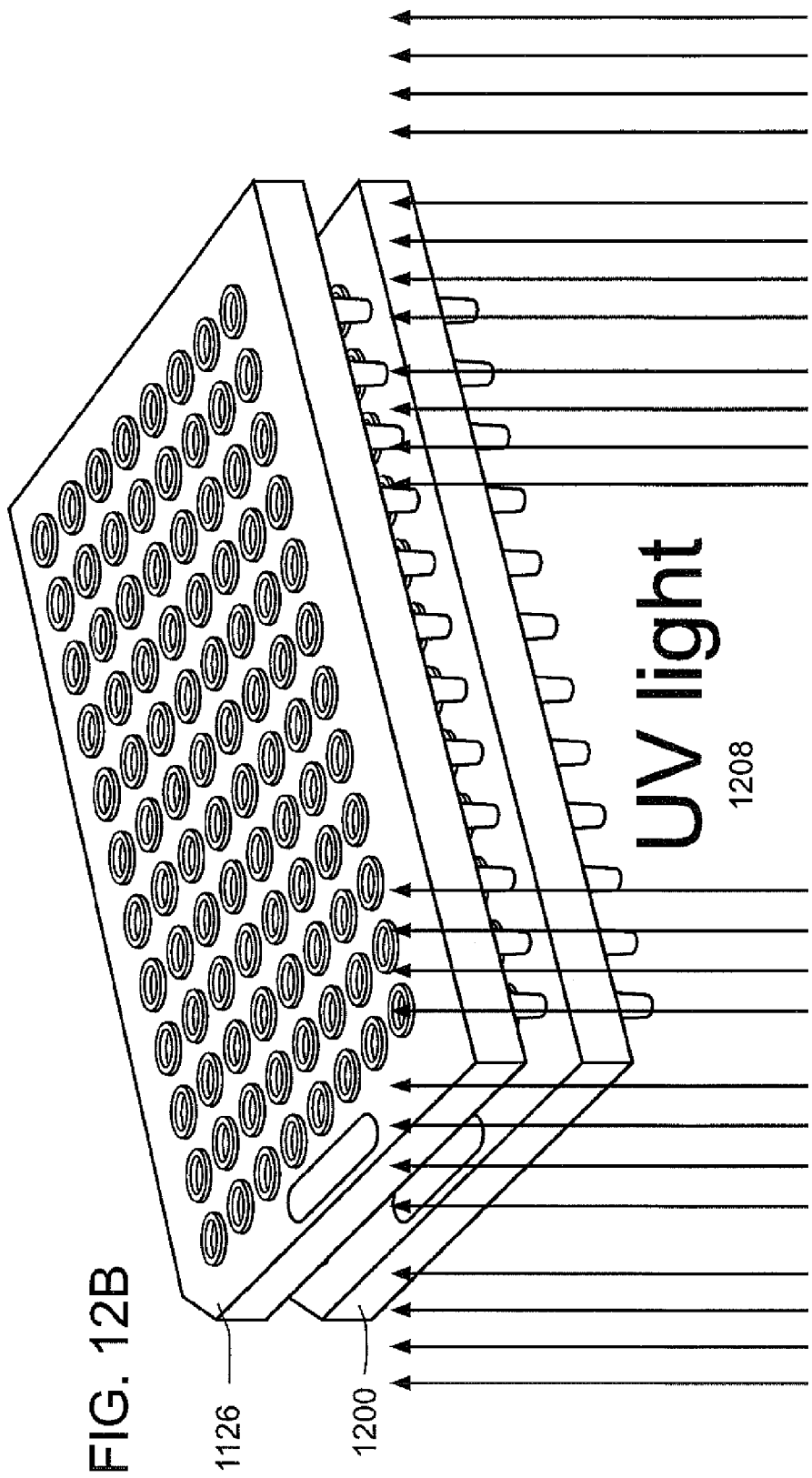

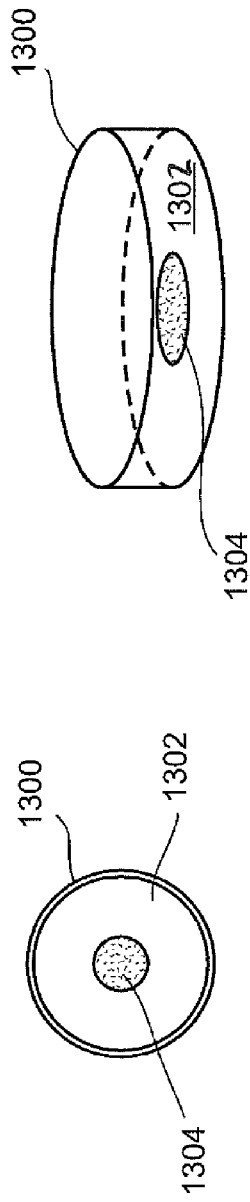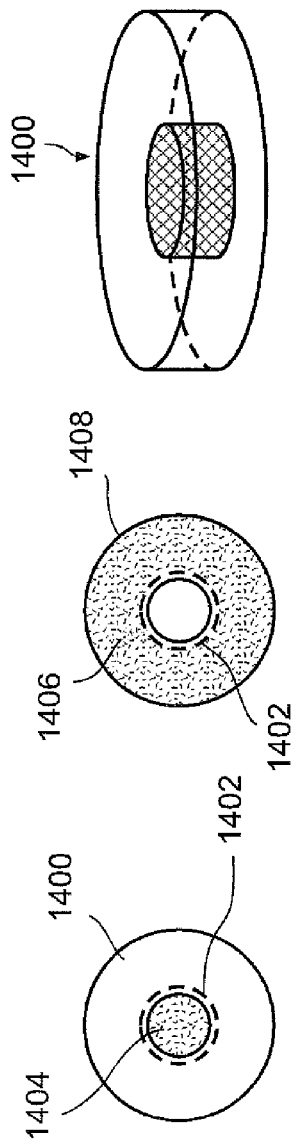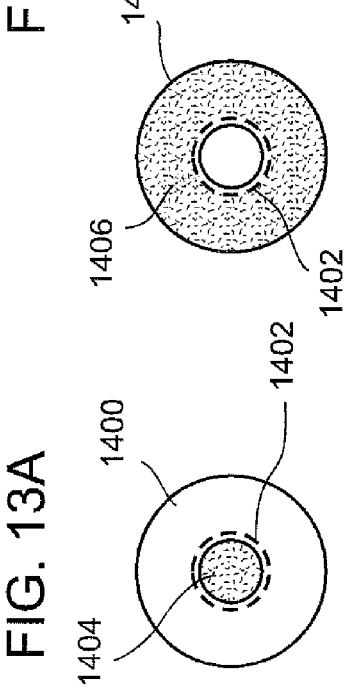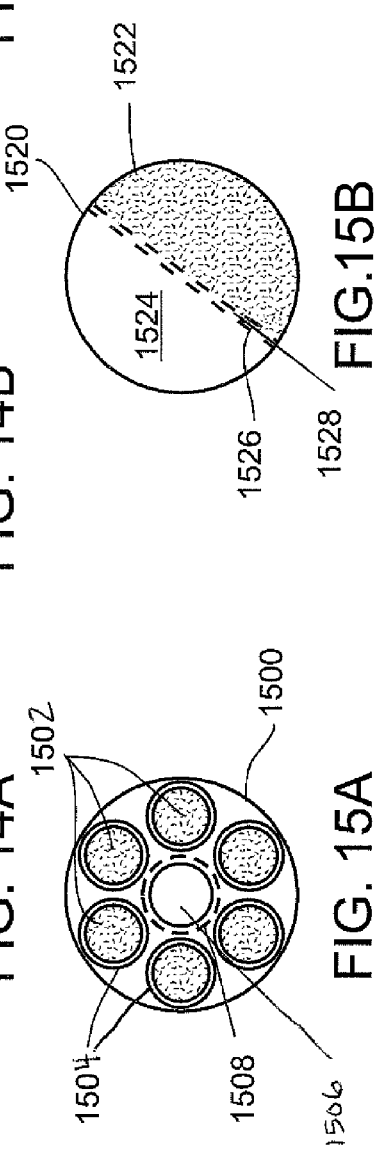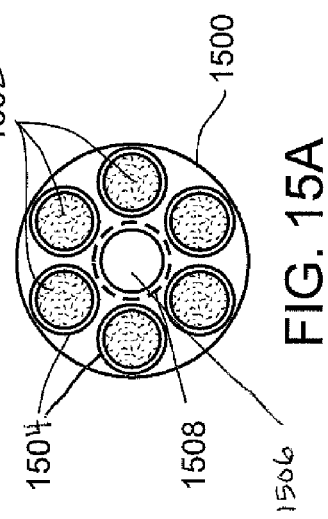
FIG. 13A  FIG. 13B  FIG. 14A  FIG. 14B  FIG. 14C  FIG. 15A  FIG. 15B

PICOLITER WELL HOLDING DEVICE AND METHOD OF MAKING THE SAME

RELATED APPLICATIONS

This application is a National Phase of PCT Patent Application No. PCT/IL2008/001492 having International filing date of Nov. 13, 2008, which is a continuation of pending U.S. patent application Ser. No. 11/940,996, filed on Nov. 15, 2007, and which also claims the benefit of U.S. Provisional Patent Application No. 61/006,130, filed on Dec. 26, 2007.

Pending U.S. patent application Ser. No. 11/940,996 a continuation-in-part of pending U.S. patent application Ser. No. 10/561,839, filed on Jun. 5, 2006, which is a National Phase of PCT Patent Application No. PCT/IL2004/000571, filed on Jun. 27, 2004, which claims the benefit of U.S. Provisional Patent Application No. 60/544,357, filed on Feb. 17, 2004, U.S. Provisional Patent Application No. 60/544,356, filed on Feb. 17, 2004, U.S. Provisional Patent Application No. 60/517,073, filed on Nov. 5, 2003, U.S. Provisional Patent Application No. 60/517,084, filed on Nov. 5, 2003, U.S. Provisional Patent Application No. 60/488,408, filed on Jul. 21, 2003, and U.S. Provisional Patent Application No. 60/482,437, filed on Jun. 26, 2003.

Pending U.S. patent application Ser. No. 11/940,996 is also a continuation-in-part of PCT Patent Application No. PCT/IL06/001487, filed on Dec. 26, 2006, which claims the benefit of U.S. Provisional Patent Application No. 60/754,216, filed on Dec. 28, 2005.

The contents of the above applications are incorporated herein by reference in their entirety.

CROSS-REFERENCE TO RELATED APPLICATIONS

This application is a continuation-in-part of U.S. patent application Ser. No. 10/561,839, filed Jun. 27, 2004, which claims the benefit of International Application No. PCT/IL2004/000571, filed Jun. 27, 2004, provisional Application No. 60/544,357, filed Feb. 17, 2004, provisional Application No. 60/544,356, filed Feb. 17, 2004, provisional Application No. 60/517,073, filed Nov. 5, 2003, provisional Application No. 60/517,084, filed Nov. 5, 2003, provisional Application No. 60/488,408, filed Jul. 21, 2003, and provisional Application No. 60/482,437, filed Jun. 26, 2003. This application is also a continuation-in-part of International Application No. PCT/IL06/001487, filed Dec. 26, 2006, which claims the benefit of provisional Application No. 60/754,216, filed Dec. 28, 2005.

This application also claims the benefit under 35 USC 119(e) of a provisional application filed on Dec. 26, 2007 and titled Device for the Study of Living Cells.

This application is also a continuation-in-part of a US application with same title and same inventors and filed on Nov. 15, 2007.

This application is also a continuation-in-part of a U.S. application Ser. No. 11/660,783, based on PCT application serial number PCT/IL2005/000914, published as US publication number 2008/0009051 on Jan. 10, 2008.

The present invention, in some embodiments thereof, relates to devices that include pico liter wells used in the study of cellular biology. More specifically, in some embodiments, there are provided holding devices having a multiplicity of pico liter wells formed in a substrate having a refractive index similar to that of water, and methods of making the same. In some embodiments, there are provided embossing or embossing-like methods.

BACKGROUND OF THE INVENTION

In the study of cellular biology, biochemistry, pharmacology, immunology, and other biological science related fields, whole, living, individual and small groups of cells are studied by manipulating and isolating the cells.

In holding devices which have substrates with pico liter wells formed in the substrate surface to trap individual cells have been available, optical artifacts may be caused by the differences between the refractive indices of the medium (typically an aqueous buffer composed largely of water) carrying the cells and the material forming the pico liter wells. Such artifacts may be caused by the refraction of light passing from the substrate to the cell carrying medium.

SUMMARY OF THE INVENTION

An aspect of some embodiments of the invention relates to a method of forming a cell holder by embossing. In an exemplary embodiment of the invention, a base is covered with an optionally liquid substrate, contacted with a die and the substrate is at least partially hardened. Optionally, the die defines a plurality of pico liter wells in the substrate. Optionally, the substrate is adhesive to the base, but not to the die, optionally in spite of the substrate being smooth and the die having small features. Optionally, the die and adhesive and base materials are selected to afford such differential adhesion. Optionally, the die is removed before the substrate hardens. In an exemplary embodiment of the invention, at least two areas on the substrate are patterned, each with a different final pattern.

In an exemplary embodiment of the invention, one or more walls or barriers are added to the cell holder before, during or after embossing.

In an exemplary embodiment of the invention, the base is not mechanically prepared for the substrate.

It is an object of some embodiments of the invention to provide a holder device having at least one cavity for receiving a sample of cells in a medium, wherein the at least one cavity includes a substrate having refractive index substantially equal to that of water, includes a multiplicity of pico liter wells (also called "picowells", herein) formed therein and has a generally inert wall.

It is an object of some embodiments of the invention to provide a method of making a holding device having a substrate characterized by an index of refraction essentially equal to that of water, which is adhered to a carrier plate, wherein the substrate is formed into a multiplicity of pico liter wells.

It is an object of some embodiments of the invention to provide a method of making a holding device having at least one cavity for receiving a medium, wherein the at least one cavity has a multiplicity of pico liter wells formed in a substrate having a refractive index substantially equal to the medium in which the cells are carried.

It is an object of some embodiments of the invention to provide a method of making a die for forming an array of picowell arrays. Optionally, the die is assembled from individual well forming die elements. Optionally, a handle with a plurality of clamps to hold the die elements is used. In other embodiments, other means to hold die elements together into a template are used. Optionally, the die also serves as a template for non-well embossed elements.

It is an object of some embodiments of the invention to provide cell holding devices including a plurality of picowell arrays, on each one, optionally in the form of a macroscopic array of picowell arrays. Optionally, the picowell arrays are separated by barriers which may have selected blocking ability, for example, being fluid blocking or cell blocking or fluid passing.

A holding device for studying cells in a medium in accordance with an exemplary embodiment of this invention comprises at least one cavity defined by generally inert wall surrounding a substrate. The substrate has a surface in which a plurality of pico liter wells is formed. The substrate is translucent and has a refractive index substantially equal to the refractive index of the medium.

An exemplary holding device for studying cells in accordance with an exemplary embodiment of this invention comprises a substantially transparent substrate having a refractive index of 1.33. The substrate has a multiplicity of pico liter wells formed in an upper surface and a wall structure attached thereto.

In another embodiment, an exemplary embodiment of the present invention includes a holding device for studying cells comprising a substantially transparent carrier plate having a plurality of cavities surrounded by walls formed in a first surface of the carrier plate, a layer of adhesive, which is known to those skilled in the art, disposed on a bottom surface of each cavity, a layer of substantially transparent substrate material having a refractive index of 1.33 and having a multiplicity of pico liter wells formed in an upper surface thereof disposed on the adhesive layer. While MY-133 is known to have a refractive index close to that of water, heretofore MY-133 has apparently not been considered suitable for use as an inert substrate for holding live cells in a medium. In other embodiments, other adhesive materials, possibly with other refractive indexes are used for embossing.

The invention, in some embodiments thereof, includes a method of making a holding device for studying cells comprising providing a layer of curable substrate, disposing a wall structure on the layer of curable substrate, embossing a multiplicity of pico liter wells in a surface of the curable substrate, and curing the substrate.

The invention, in some embodiments thereof, includes a method of making a holding device for studying cells comprising providing a carrier plate, applying a first adhesive layer to the carrier plate, depositing a curable substrate on the adhesive layer, applying a second layer of adhesive to the substrate, attaching a wall structure to the second layer of the adhesive, forming a multiplicity of pico liter wells in the substrate with a template, curing the substrate, and removing the template.

The invention, in some embodiments thereof, also includes a method of making a holding device comprising providing a carrier plate having a plurality of cavities surrounded by walls, depositing a curable substrate in each cavity, embossing a multiplicity of pico liter wells in the curable substrate with a die, and curing the substrate.

As used herein, the term "embossing" includes contacting a substrate with a die and then causing the substrate to set in its new form, for example, by UV curing, radiation curing, chemical curing, hardening and/or cooling. In an exemplary embodiment of the invention, the setting is at room temperature using UV curing, which optionally reduces distortions.

There is provided in accordance with an exemplary embodiment of the invention, a holding device for studying cells comprising a plurality of spaced apart pico liter well arrays.

In an exemplary embodiment of the invention, said pico liter well arrays comprise embossed regions. Optionally or alternatively, the device comprises at least one barrier between two pico liter well arrays.

In an exemplary embodiment of the invention, said arrays are arranged in a two dimensional repeating pattern.

In an exemplary embodiment of the invention, said arrays include at least two different well array designs.

In an exemplary embodiment of the invention, said device includes at least one non-well embossed region fluidically connected to at least one of said arrays.

There is provided in accordance with an exemplary embodiment of the invention, a holding device for studying cells comprising at least two defined regions:

(a) a pico liter well array region including a plurality of pico liter wells; and (b) a non cell holding region in fluid communication with said pico liter well region, wherein fluid can be one or both of added and removed from said non cell holding region without disturbing cells in said picowells.

In an exemplary embodiment of the invention, the device comprises at least one fluid permeable barrier between said regions.

In an exemplary embodiment of the invention, said non-cell holding array has an embossed design. Optionally or alternatively, said pico liter well array is embossed.

In an exemplary embodiment of the invention, the device comprises a plurality of pico liter well array regions.

There is provided in accordance with an exemplary embodiment of the invention, a method of forming a template for a picowell array, comprising:

(a) providing a form defining thereon a plurality of pico liter wells;

(b) applying at least one apertured spacer above said form;

(c) contacting said form with a settable material through said apertured spacer; and (d) removing said spacer and said set material from said form In an exemplary embodiment of the invention, the method comprises assembling a plurality of said set material into a composite template for embossing a cell holding device.

There is provided in accordance with an exemplary embodiment of the invention, a method of forming a cell holding device with at least one pico liter well array, comprising:

(a) providing a base covered with a hardening material, adapted to at least indirectly adhere to said base;

(b) contacting said base with a die, said die defining at least one pico liter well region and said die adapted to not adhere to said hardening material; and (c) at least partially hardening said hardening material while in contact with said die.

In an exemplary embodiment of the invention, the method comprises further hardening said hardening material after removal of said die.

Optionally or alternatively, the method comprises priming said base before covering with said hardening material.

In an exemplary embodiment of the invention, said hardening material is a liquid UV curable adhesive. Optionally, said UV curable adhesive has an index of refraction within 5% of that of water.

In an exemplary embodiment of the invention, said base is not mechanically abraded under said substrate.

In an exemplary embodiment of the invention, the method comprises forming at least one barrier between said region and other parts of said base.

In an exemplary embodiment of the invention, said barrier is formed on said base before said contacting.

In an exemplary embodiment of the invention, said barrier is formed on said base during said contacting.

In an exemplary embodiment of the invention, said die defines a plurality of spaced apart pico well regions.

In an exemplary embodiment of the invention, said die defines a plurality of different embossing patterns to be embossed on said hardening material simultaneously.

There is provided in accordance with an exemplary embodiment of the invention, a holding device for studying cells comprising:

at least one cavity adapted to receive a sample of cells in a medium consisting essentially of water, the cavity having a substrate and a generally inert wall, wherein the substrate includes a surface for receiving the medium, and wherein the surface includes a multiplicity of pico liter wells and is characterized in that the substrate is substantially translucent and has a refractive index equal to the refractive index of the medium.

In an exemplary embodiment of the invention, the medium comprises water and wherein the substrate has a Refractive Index of 1.33.

In an exemplary embodiment of the invention, the substrate is moldable.

In an exemplary embodiment of the invention, the substrate is inert.

In an exemplary embodiment of the invention, the holding device is a carrier plate, and wherein a first adhesive is disposed between the carrier plate and the substrate. Optionally, the device comprises a second adhesive disposed between the generally inert wall and the substrate. Optionally, at least one of the substrate, the first adhesive and the second adhesive are UV-light curable. Optionally or alternatively, the first adhesive and the second adhesive are acrylic. Optionally or alternatively, the device comprises a light source transmitting the UV-light through a bottom surface of the at least one cavity.

In an exemplary embodiment of the invention, the substrate is exposed to the UV-light under vacuum pressure. Optionally, the vacuum pressure is in the range of 0.3-0.5 mmHg.

In an exemplary embodiment of the invention, the substrate is exposed to the UV-light under inert gas.

There is provided in accordance with an exemplary embodiment of the invention, a method of making a holding device for studying cells, comprising:

providing a carrier plate;
applying a first adhesive layer to the carrier plate;
depositing a curable substrate on the adhesive layer;
applying a second layer of adhesive to the substrate;
attaching a wall structure to the second layer of adhesive;
forming a multiplicity of pico liter wells in the substrate with a template;
curing the substrate; and
removing the template.

In an exemplary embodiment of the invention, curing the substrate includes exposing the substrate to UV-light through the carrier plate.

In an exemplary embodiment of the invention, the method comprises repeating curing the substrate after removing the template, wherein curing the substrate after removing the template includes exposing the substrate to UV-light under a vacuum pressure through the carrier plate.

In an exemplary embodiment of the invention, forming a multiplicity of pico liter wells in the substrate with a template further comprises embossing a surface of the substrate with a die.

There is provided in accordance with an exemplary embodiment of the invention, a method of making a holding device, comprising:

providing a layer of curable substrate;
disposing a wall structure on the layer of curable substrate;
embossing a multiplicity of pico liter wells in a surface of the curable substrate; and
curing the substrate.

In an exemplary embodiment of the invention, the method comprises disposing a first adhesive between the curable substrate and the wall structure.

In an exemplary embodiment of the invention, curing the substrate comprises exposing the substrate to the UV-light through the carrier.

There is provided in accordance with an exemplary embodiment of the invention, a method of making a holding device for studying cells comprising:

providing a carrier plate having a plurality of cavities surrounded by walls;
depositing a curable substrate in each cavity;
embossing a multiplicity of pico liter wells in the curable substrate with a die; and
curing the substrate.

In an exemplary embodiment of the invention, the method comprises applying a first adhesive layer in each cavity before depositing the curable substrate in each cavity.

In an exemplary embodiment of the invention, curing the substrate comprises exposing the substrate and the first adhesive to UV-light through the carrier plate when the die is in place.

In an exemplary embodiment of the invention, the method comprises removing the die and exposing the substrate to UV-light under a vacuum or inert gas through the carrier plate.

There is provided in accordance with an exemplary embodiment of the invention, a holding device for studying cells comprising:

a layer of substantially transparent substrate material having a multiplicity of pico liter wells having a refractive index of 1.33; and,
a wall structure attached to the substrate.

In an exemplary embodiment of the invention, the substrate is UV-light curable.

In an exemplary embodiment of the invention, the device comprises a first adhesive disposed between the wall structure and the substrate.

In an exemplary embodiment of the invention, the device comprises a substantially transparent carrier plate having a plurality of cavities surrounded by walls formed in a first surface of the carrier plate, wherein the layer of substantially transparent substrate material is disposed on the carrier plate.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIGS. 11A-11C illustrate a method of forming an embossing die, in accordance with an exemplary embodiment of the invention;

FIGS. 12A-12C illustrate a method of forming an array of pico liter well arrays, in accordance with an exemplary embodiment of the invention;

FIGS. 13A and 13B illustrate a Petri-dish with an isolated pico liter well array formed thereon, in accordance with an exemplary embodiment of the invention;

FIGS. 14A-14C illustrate Petri-dish designs with one or more pico liter well arrays and with a partitioning element, in accordance with an exemplary embodiment of the invention;

FIGS. 15A and 15B illustrate Petri-dish designs with multiple partitioning elements, in accordance with an exemplary embodiment of the invention.

DETAILED DESCRIPTION OF THE INVENTION

Figure 1:
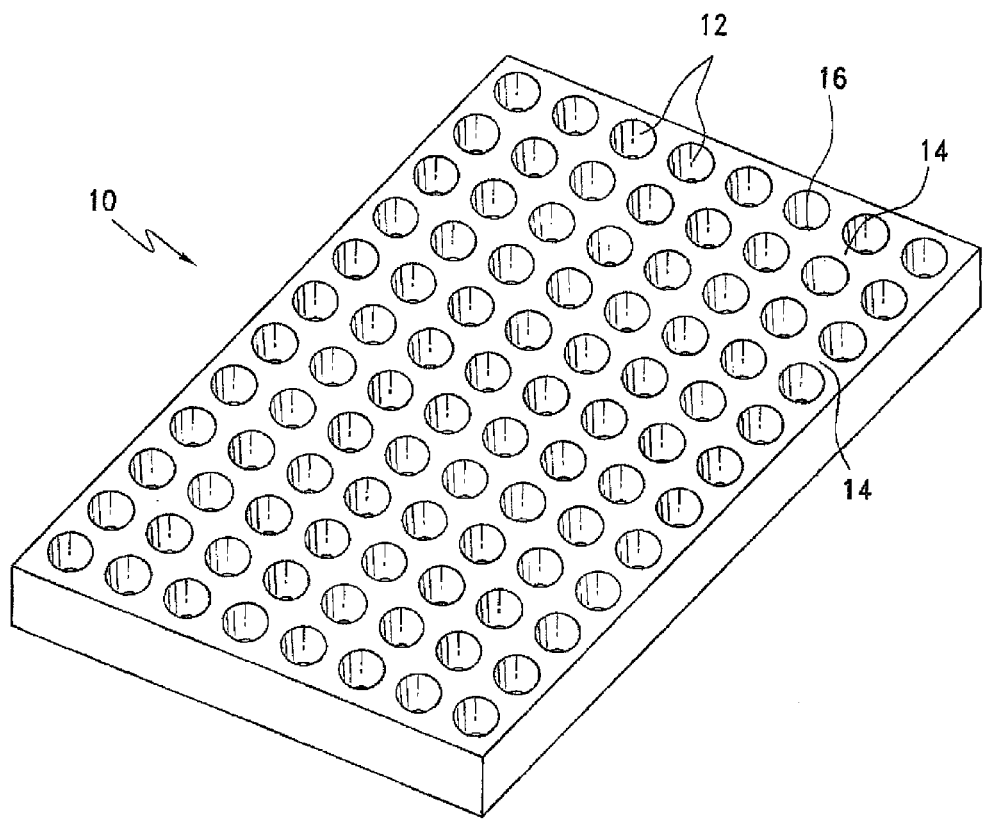
FIG. 1 is a perspective view of a presently preferred embodiment of a holding device.

The present invention, in some embodiments thereof, relates to devices that include pico liter wells used in the study of cellular biology. More specifically, in some embodiments, there are provided holding devices having a multiplicity of pico liter wells formed in or on a transparent, non-cytotoxic substrate, optionally, but not necessarily having a refractive index similar to that of water, and methods of making the same. In some embodiments, there are provided embossing methods.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the figures, FIG. 1 is a perspective view of a holding device 10 having at least one cavity 12. Holding device 10 may be a Petri dish or similar device, or an assay plate having 6, 12, 48, 96, 384, or 1536 cavities and a standard 8.5 cm by 12.5 cm footprint. The cavity or plurality of cavities 12 is configured to receive aliquots of cells that are temporarily suspended in a desired medium, such as a buffered medium comprising mostly water. The diameter of the individual cavities 12 depends on the number of wells included on the holding device 10. Optionally, the cavities 12 of a 1536 well plate have a diameter greater than approximately 250 micrometers. It should be apparent that the volume of the cavities 12 also depends on the number of cavities and on the depth of each cavity. In some examples, the volume of each cavity is greater than $5 \times 10^{-6}$ liters. In other embodiments, the cavities are designed to hold groups of cells, cell clusters, embrionic bodies, interacting cells and/or oocytes, for example, which may affect the desired geometry and/or volume of the picowells. For example, 100 micron diameter wells may be designed as deep wells, in order to accommodate one large cells spheroid, or alternatively, as a shallow pan, in order to explore group of small cells (e.g. lymphocytes, yeast cells) while maintaining them in a same focal plane of a microscope. Exemplary well diameters include 1 micron, 5 microns, 10 microns, 30 microns, 60 microns, 100 microns and 250 microns and smaller, intermediate or large sizes may be provided as well. Exemplary depths include 1 micron, 5 microns, 10 microns, 30 microns, 60 microns, 100 microns and 250 microns and smaller, intermediate or large sizes may be provided as well.

Figure 9:
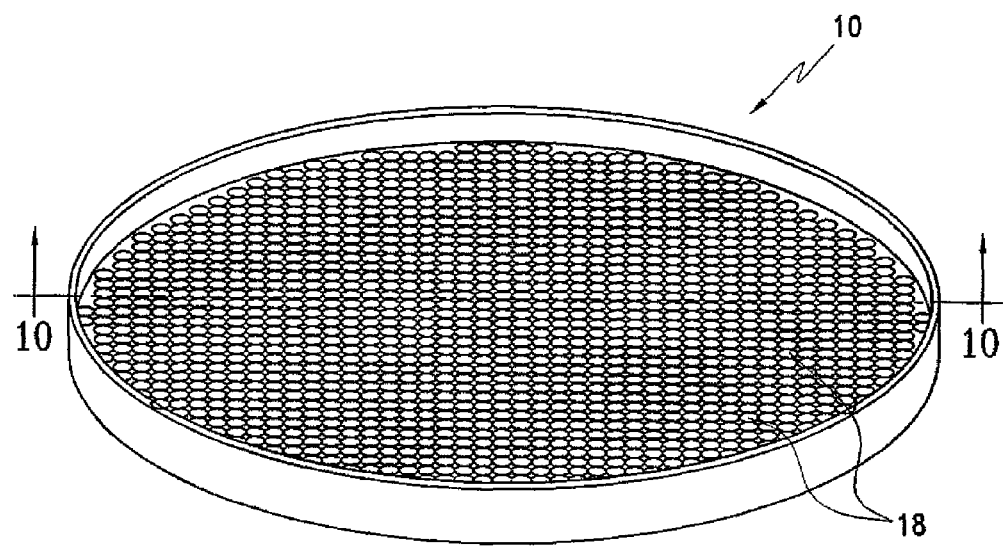
FIG. 9 is a perspective view of a Petri-dish having the plurality of pico liter wells formed in the substrate.

The cavities 12 optionally further include generally inert walls 14 (also referred to hereinafter as a plurality of walls or a wall structure) and a bottom substrate 16 having a multiplicity of pico liter wells 18 (as shown in FIG. 9). Optionally, the pico liter wells 18 are configured to physically confine individual cells or a group of cells, wherein the diameter of the pico liter wells 18 depends on the size of the cells to be used. For example, the cells optionally have a diameter between about 5 and 250 micrometers and the pico liter well size and shape may correspond thereto.

Figure 2:
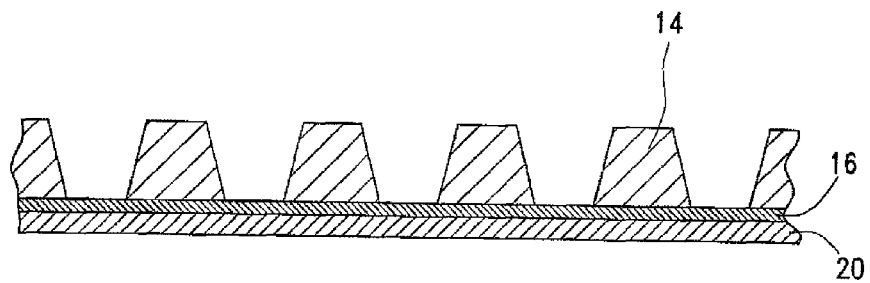
FIG. 2 is a cross-sectional view of a carrier plate having a substrate and a plurality of walls.
Figure 3:
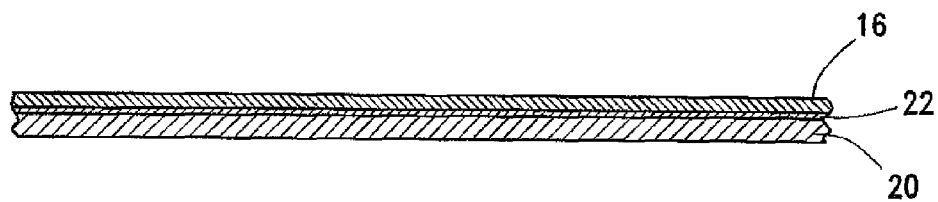
FIG. 3 is a cross-sectional view of the carrier plate having a first adhesive and the substrate applied thereon.

In an embodiment of the invention, the substrate 16 is curable, moldable and inert. The substrate 16 in the cured state has an index of refraction of 1.33, which has the substantially same index of refraction as water and approximately the same index of refraction of most mediums used for suspending cells. Optionally, the substrate 16 is MY-133, which is a commercially available material and can be purchased at My Polymers LTD at www.mypolymers.com/Default.htm. In potential advantage to Du-Pont low refractive index fluoropolymers resins and films (www2.dupont.com/Teflon_Industrial/en_US/products/product_by_name/teflon_fep/index. html), the MY-133 is a UV-curable fluoropolymer. In other embodiments, the material used is different and/or does not have the same refractive index as water. However, the same process is optionally applied. In an exemplary embodiment of the invention, the substrate is selected to not adhere to the die. Following are exemplary pairs of substrate/die materials, where the substrate can adhere directly or indirectly to a transparent base and avoid adhering to the die:

(a) My-133/glass, My133/metal (e.g. nickel),
(b) NOA/PDMS, 3M 3321 (medical grade optically clear adhesive)/PDMS
(c) NOA/Parylene™ coated metal or glass die, 3M 3321/Parylene™ coated metal or glass die As shown in FIG. 2, in an embodiment of the invention, the substrate 16 is applied to a carrier plate 20, optionally by brushing, stamping or printing the substrate 16 thereon. The carrier plate 20 is optionally made from glass or another optically transmissive material such as polystyrene, polycarbonate, PMMA (Poly-methyl-metacrilate). Optionally, a material is chosen which has optical transparency at least at wavelengths used for visual and/or florescent inspection (e.g., near IR, far IR or near UV) and/or has a refractive index at those wavelengths that is within 20%, 10%, 5%, 1%, 0.1 or intermediate amounts of the refractive index of the aqueous medium used, for example, of that of water with 0.9% salts and sugars added (e.g., to within those percentages of 1.33).

In order to improve the adherence of and/or prevent optical artifacts at the interface therebetween the substrate 16 to the glass carrier plate 20, the carrier plate 20 is optionally pretreated with silane before the substrate 16 is applied. The silanation of the surface of the carrier plate 20 can be performed in a manner known to one skilled in the art. Through such silanation process, acrylic groups are attached by covalent bonds to the glass, improving the adhesion of the substrate 16 to the glass carrier 20. Other intermediate base layers may be applied, especially if substrate 16 is of another formulation. Optionally or alternatively, Plasma or Corona treatment (e.g., as described at www.tantec.com) may used in some cases. Optionally or alternatively, mechanical abrasion is provided. In an exemplary embodiment of the invention, however, plate 20 is kept smooth.

The substrate 16 forms a layer, which may have a thickness of less than 200 microns and more optionally in the range of 80-120 microns. Other thicknesses may be provided as well, for example, as described below: between 10 and 300 microns for example, for example, slightly more than the depth of the pico liter wells or other structures embossed. The plurality of walls 14 is optionally then disposed on the substrate 16.

Pico liter well forming templates 26 are disposed between each set of plurality of walls 14 disposed on the substrate 16 layer and are pressed into the substrate 16. The templates 26 are optionally dies capable of embossing the substrate 16 with pico liter sized wells. The layered configuration, including the carrier plate 20, the substrate 16, the templates 26 pressed into the substrate 16, and the plurality of walls 14 is polymerized by UV-radiation to cure the substrate 16. Optionally, the layered configuration is irradiated with UV-light through the bottom of the translucent carrier plate 20. The templates 26 are then optionally removed and the holding device 10 is cured again by irradiating the holding device 10 with UV-light under a vacuum of 0.3-0.5 mmHg. An exemplary method of forming such dies is shown with respect to FIGS. 11A-11C, below. In an exemplary embodiment of the invention, a short, uniform exposure, or precure, is used as a first curing step. The precure time is optionally selected to be of sufficient duration to set the bond and allow the substrate and/or die to be moved without disturbing alignment. This is followed by a longer cure under UV light to obtain full cross-linking and solvent resistance of the adhesive.

In an alternative embodiment of the invention, as shown in FIGS. 3-6, the holding device 10 includes at least a first adhesive 22 applied between the carrier plate 20 and the substrate 16 to further improve bonding of the substrate 16 thereto. Additionally, a second adhesive 24 may be applied to further improve bonding of the plurality of walls 14 to the substrate 16. An exemplary holding device 10 and method of making the same is described herebelow.

In order to improve the adherence of the adhesive 22 to the glass carrier plate 20, the carrier plate 20 is optionally pretreated with silane before the first adhesive 22 is applied. The silanation of the surface of the carrier plate 20 can be performed in a manner known to one skilled in the art. Through such silanation process, acrylic groups are attached by covalent bonds to the glass, improving the adhesion of the first adhesive 22 to the glass carrier 20. Other treatments as described herein may be applied as well.

A thin coat of the first adhesive 22 is applied to the carrier plate 20, optionally, by brushing the adhesive 22 thereon. It should be apparent, however, that other techniques may be used to apply the first adhesive 22, such as by stamping, printing, spraying, dipping, wiping, or the like. Optionally, the adhesive 22 is applied to only those locations that correspond to the locations of the plurality of walls 14, such that the transparency of the bottom of each cavity 12 is not affected by the adhesive 22. However, in an embodiment of the invention, the adhesive 22 comprises mostly MY-133 and can be applied to the entire surface of the carrier plate 20 because the adhesive 22 also has substantially the same refractive index as water. The adhesive 22 can be any type of adhesive that bonds to the substrate as described below. Optionally, the first adhesive is a viscous primer that does not mix into a substrate 16. More specifically, the first adhesive 22 is applied as a dilute solution of 25% solids in a mixture based on a medium boiling solvent, wherein the solvent evaporates leaving a thin, but highly viscous layer of adhesive 22 on the carrier plate 20. The solvent optionally comprises PCBTF (also know by the trade name of Oxsol 100), having a boiling point of 139 degrees, isopropyl alcohol (IPA) and acetone. Optionally the adhesive 22 is an ultraviolet (UV) radiation curable formulation which adheres well to the substrate 16 and the carrier plate 20. Optionally, the adhesive 22 is selected so that it is polymerized together with the substrate 16 when exposed to ultraviolet radiation. Optionally, the adhesive 22 is applied to the carrier plate 20 and the substrate 16 is applied over the adhesive 22, the combination polymerized by UV-radiation at the same time. In an exemplary embodiment of the invention, the adhesive is a combination of both a fluoropolymer and a acrylic agent. The acrylic agent bonds well to the glass or plastic bottom, whereas the fluoropolymer bonds the MY-133 layer. Therefore, the adhesive serves as an intermediate layer which connects the My-133 with the bottom later. Optionally, the layer used is formed of primer-133 available from My polymers LTD of Rehovot Israel. Primers G and P may also be used, possibly with reduced optical efficacy.

Further coats of the adhesive 22 can be applied to the first coat of the adhesive 22 and each coat is allowed to dry for optionally at least 2-4 minutes. Optionally, this delay is selected to allow for the creation of longer and/or more entangled polymer chains, so bonding becomes stronger.

The substrate 16 is applied to the adhesive 22 coated surface of the carrier plate 20 and is formed from a moldable optionally UV curable material optionally having an index of refraction substantially the same as the index of refraction of a buffered, substantially water-based medium, for example, Du-Pont Teflon FEP I or MY-133. The substrate 16 forms a layer, which may have a thickness of less than 200 microns and optionally in the range of 80-120 microns. Optionally, the layer is made thinner due to cost considerations and/or for improved optical ability (e.g., limited depth range of microscope), while maintaining a minimal mechanical strength for its intended application.

Optionally, when the substrate 16 is formed from MY-133, the adhesive comprises a polymer that optionally includes both acrylic groups and highly fluorinated groups that attract the components of the MY-133. Where a glass carrier plate 20 is used, it may be desirable to modify the first adhesive 22 to increase its affinity for glass. The adhesive 22 thus, may include 1-2% additional silane.

A second adhesive 24 (optionally of a mixture of acrylic and fluorocarbon polymer precursors) is optionally applied to the bottom of the plurality of walls 14 arranged to define cavities 12 of the holding device 10 and the plurality of walls 14 are then disposed onto the substrate 16. The second adhesive 24 is allowed to dry for at least 2-4 minutes, or as needed. Similar to the first adhesive 22, the second adhesive 24 is also a viscous primer that does not mix into a substrate 16. More specifically, the second adhesive 24 is optionally applied as a dilute solution of 25% solids in a mixture based on a medium boiling solvent, wherein the solvent evaporates leaving a thin, but highly viscous layer of adhesive 24 on the bottom of the plurality of walls 14. The solvent optionally comprises PCBTF (also known by the trade name Oxsol 100), having a boiling point of 139 degrees, isopropyl alcohol (IPA) and acetone. Optionally the adhesive 24 is an UV-radiation curable formulation which adheres well to the substrate 16 and the plurality of walls 14. Optionally, the adhesive 24 is selected so that it is polymerized together with the substrate 16 when exposed to ultraviolet radiation. This permits the adhesive 24 to be applied to the bottom of the plurality of walls 14, which is then attached to the substrate 16 layer adhered to the carrier plate 20 by the first adhesive 22.

It should be appreciated by those having ordinary skill in the art that although the above-described adhesives are described, other adhesives that are capable of bonding to the substrate 16 can be used.

Figure 4:
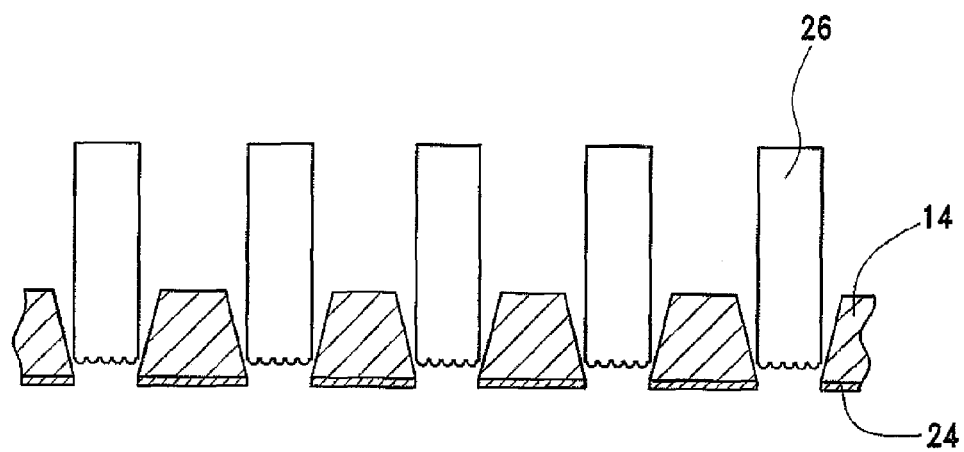
FIG. 4 is a cross-sectional view of the plurality of walls and templates.
Figure 5:
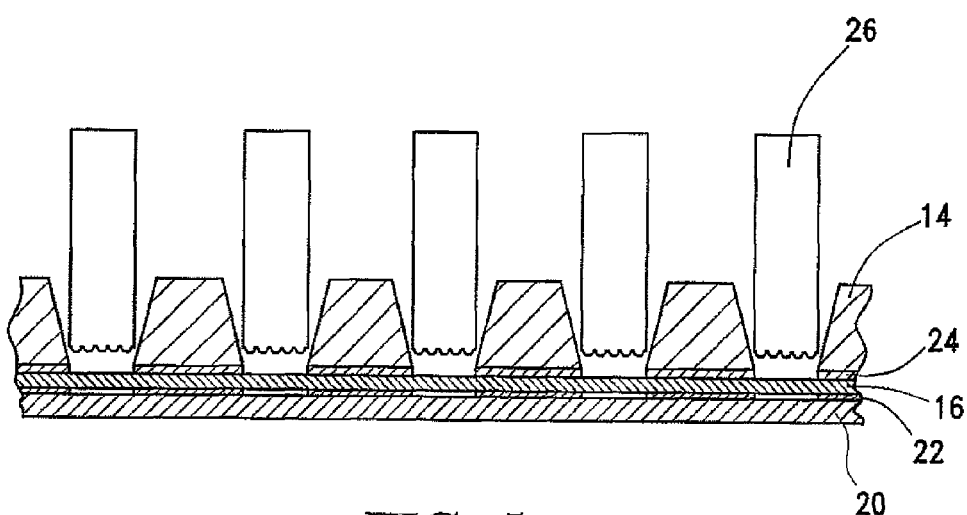
FIG. 5 is a cross-sectional view of the holding device showing the plurality of walls mounted on the carrier plate and showing dies embossing a plurality of pico liter wells in the substrate.
Figure 6:
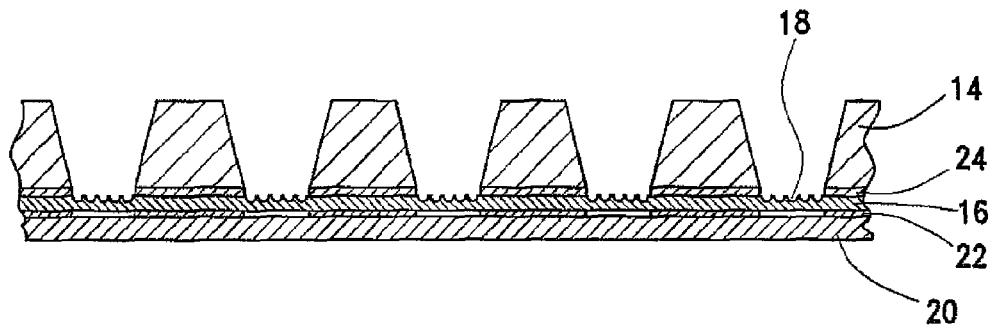
FIG. 6 is a cross-sectional view of the holding device showing the pico liter wells embossed in the substrate.

As shown in FIGS. 4 and 5, pico liter well forming templates 26 (or a single multi-fingered template) are disposed between each set of plurality of walls 14 disposed on the substrate 16 layer and are then pressed into the substrate 16. The templates 26 are optionally dies capable of embossing the substrate 16 with pico liter sized wells. In an exemplary embodiment of the invention, the substrate is liquid so the dies need to only be strong enough to support their own weight as little pressure is optionally applied. Optionally, the use of low pressure is to avoid damage and/or distortion to underlying plate and/or setting substrate. The layered configuration, including the carrier plate 20, first adhesive 22, substrate 16, template pressed into the substrate 16, and plurality of walls 14 is polymerized by UV-radiation to cure the substrate 16 and the adhesives 22, 24 at the same time. Optionally, the layered configuration is irradiated with UV-light through the bottom of the translucent carrier plate 20. Optionally, this curing is sufficient to set the adhesives so the die can be removed, but does not finish hardening the substrate. The templates 26 are then optionally removed and the holding device 10 is cured again by irradiating the holding device 10 with UV-light under vacuum of 0.3-0.5 mmHg Optionally, the Vacuum is used to avoid chemical interference of oxygen with the setting material. Optionally or alternatively, an inert gas is used instead of vacuum. While not required for some adhesives, in others, washing with ethanol to remove toxic precursor materials may be useful.

Figure 7:
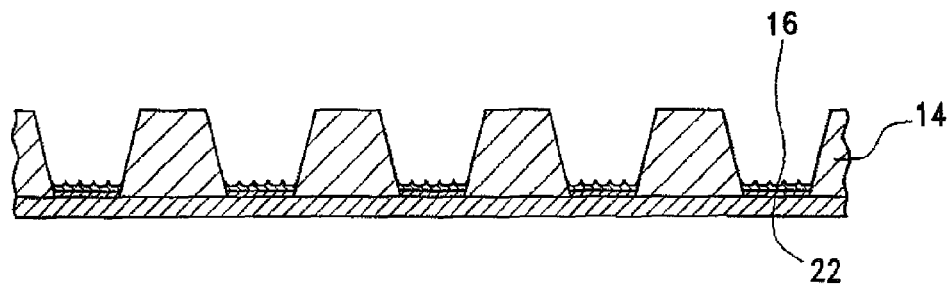
FIG. 7 is a cross-sectional view of the holding device showing the first adhesive and the substrate applied to the bottom of cavities.
Figure 8:
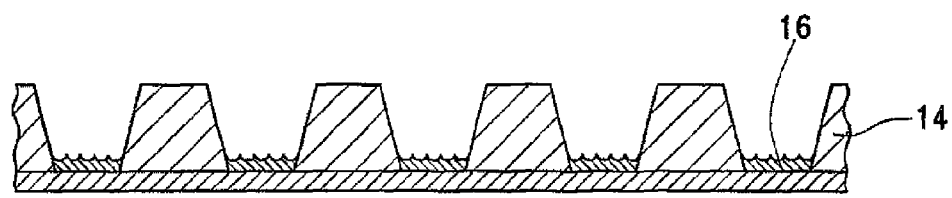
FIG. 8 is a cross-sectional view of the holding device showing the substrate applied to the bottom of the cavities.

Another method of making some embodiments of the invention includes providing a carrier 20 having at least one cavity 12 surrounded by walls 14. As shown in FIG. 7, a layer of either the first or second adhesive 22, 24, respectively, is deposited at the bottom of the at least one cavity 12. A layer of substrate 16 is then applied to the adhesive layer 22 or 24. The layer of substrate 16 can also be applied directly to the bottom of the at least one cavity 12, without the adhesive 22 or 24 as shown in FIG. 8. The pico liter well templates 26 are then translated between the walls 14 and pressed into the substrate 16 to emboss the pico liter wells 18. The first or second adhesive 22 or 24, if present, and the substrate 16 are cured by UV-radiation through the bottom of the holding device 10. Then, the templates 26 are removed and the holding device 10 undergoes further curing by UV-light under vacuum of 0.3-0.5 mmHg or inert gas.

Figure 10:
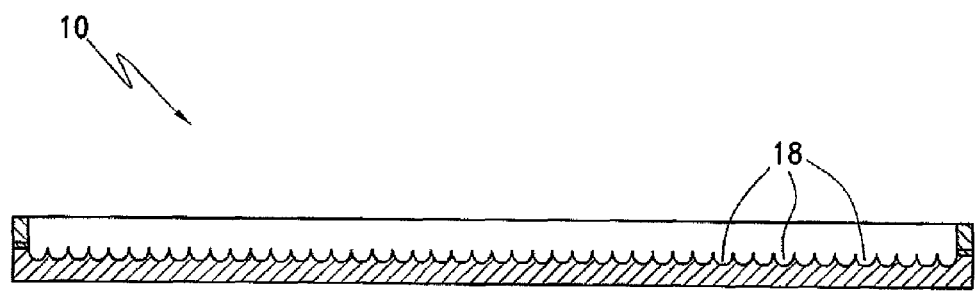
FIG. 10 is a cross-sectional view of the Petri-dish having the plurality of pico liter wells formed in the substrate.

In yet another embodiment of the invention, a separate carrier plate 20 is not utilized. That is, the holding device 10 can include the substrate 16 embossed to form pico liter wells 18 as described above and shown in FIGS. 9 and 10. The substrate 16 optionally has a thickness of less than 200 microns and more optionally in the range of 80-120 microns. Other thicknesses may be used, for example, for mechanical considerations. The walls 14 are disposed on the substrate 16 and templates 26 are pressed into the substrate 16. While the templates remain pressed into the substrate 16, the substrate 16 is cured with UV-radiation. The templates 26 are removed and the substrate 16 can optionally be cured again, but with UV-radiation under vacuum. Alternatively, a plate 20 with a same index of refraction as substrate 16, is used. Optionally, one of the above materials is used. Optionally or alternatively, Cytop® available from Asahi Glass Ltd. (AGC group) of Tokyo Japan, is used.

In another embodiment of the invention, the walls 14 can be disposed on the substrate 16 after the UV-curing thereof. The walls 14 are then affixed along a perimeter edge of the substrate 16 using any type of strong adhesive known in the art. Optionally, barriers (see below) and/or walls are dipped in a UV adhesive (or such adhesive is brushed on) and the adhesive set during a same or separate step of UV curing as used for the embossed sections. According to one aspect of the invention, the perimeter of the walls 14 can be adhered to the edge of the substrate 16 forming a Petri dish-shaped holding device 10.

Alternatively, the walls 14 having adhesive 22 or 24 can be applied to a layer of substrate 16, wherein the substrate 16 functions as the bottom of the holding device 10. The templates 26 are pressed into the substrate 16 to emboss the pico liter wells 18 therein. The layered configuration, including the templates 26, is cured using UV-radiation. It should be appreciated by one having ordinary skill in the art that, since the holding device 10 does not include the carrier plate 20 attached to the substrate 16 via adhesive 22 or 24, the holding device 10 can be cured from above the substrate 16 or below the substrate 16. After the first curing step, the template 16 is removed and the holding device 10 is then cured again, using UV-light under vacuum. Thereafter, the pico liter well holding device 10 is optionally sterilized and/or washed for use in biological experiments. Such post-manufacture acts may be carried out with other methods of forming device 10.

In an alternative embodiment, the walls are pressed against a layer of substrate 16 at a same time as templates 26 are pressed, with the walls adhering and the templates causing embossing.

In an alternative embodiment, a base 20 has a layer of picowells formed thereon, for example, by embossing a layer of substrate 16 thereon. In one example, embossing is uses an embossing cylinder. Thereafter, the walls 14 are attached onto substrate 16, in some cases, possibly covering existing picowells thereon. Optionally, the bottom of the walls are coated with an adhesive layer of sufficient volume to fill in such picowells.

In an exemplary embodiment of the invention, spreading of substrate 16 on base 20 depends on the area being embossed. If a small area, substrate 16 is optionally applied as drops to the center of the areas to be embossed. If a larger area, substrate 16 is optionally spread using a draw bar or rollercoater. Methods known in the art for spreading such adhesives (and for bonding to other materials) may be used.

In an alternative layer, walls 14 are applied while templates 26 are embossing layer 16. Optionally, this allows the templates to protect the shape and/or cleanliness of the picowells from the adhesive and/or other process used for attaching the walls.

In an exemplary embodiment of the invention, the embossing methods described herein are applied on fragile bases so little temperature and/or pressure changes are applied. Rather the embossing is optionally at low pressure and at room temperature (e.g., 15-35 degrees Celsius). In an exemplary embodiment of the invention, the embossed substrate is non-reversibly deformed by the embossing. In an exemplary embodiment of the invention, the embossed substrate is set by one or more of chemical setting, light setting, radiation based setting and/or other cross-linking or hardening or setting methods known in the art and as appropriate for the specific materials used.

In an exemplary embodiment of the invention, the thickness of the embossed layer is minimal, for example, being 15, 5%, 20%, 60%, 100%, 300%, 100% or intermediate percentages of the depth of the picowell and/or other embossed feature. Optionally or alternatively, the additional thickness below the well is 1, 10, 20, 30, 100 microns or intermediate amounts. Variations of the embossing methods described herein, which may be variously referred to as "stamping", "micro-stamping", "replicating" or "soft-lithography" may also be practiced in accordance with some embodiments of the invention.

In an exemplary embodiment of the invention, embossing can include modification of the picowells in addition to changing the geometry. For example, the template can have attached thereto patterns for the walls between the picowells, medicaments and chemicals for attachment to the picowells or walls between them, small beads for such transfer and/or electrode wires. In portions that are not for picowells, electronics, valves and/or other items may be impressed on the substrate during embossing.

Once manufacturing is completed (or during manufacturing), device 10 can be further processed in various ways, for example, washing to remove toxic residues, hole drilling (e.g., using laser, e-beam) and/or sterilization.

In use, holding device 10 is optionally seeded with cells, for example by injecting cells suspended in a medium, such as an aqueous buffered medium, into at least a first cavity of the holding device 10. The device 10 is optionally agitated to ensure that the cells settle in the pico liter wells 18. The cells are then observed from below, for example, using a confocal microscope or brightfield microscope with or without deconvolution image processing software. Optionally or alternatively, fluorescent imaging methods are used. Because the substrate 16 has a refractive index of water, optical artifacts, which would otherwise be caused by the differences between the refractive indices of the medium carrying the cells and the substrate 16, are essentially eliminated. This gives the viewer the ability to observe the cells being studying more precisely as if there were no microstructures on the substrate.

One potential advantage of a cell holder with multiple picowell arrays is that multiple experiments which require some similar conditions and some different conditions can be conducted simultaneously. For example, incubation can be same for all well areas, while cell type and/or reagents (e.g., drugs) added could be different. Optionally or alternatively, a same experiment can be repeated in separate well areas, so that cells metabolites from one cell do not affect others. Optionally, the wells themselves are different between areas, which may also affect the outcome of such an experiment.

Other materials may also serve as the polymerizing agent as well and used to form the pico liter wells array. Even though they may not posses the unique index of refraction of water, their transparency enables the observation of cells or other microscopic particles which are carried by in the wells defined in the embossed substrate. It should be noted that, generally, the difference in index of refraction yields to the observation of the pico liter wells contours when observed in brightfield microscopy; in fluorescence microscopy the fluorescence cells or other microscopic particles emits new intrinsic light in certain range of wavelengths which is out of the range of the excitation light, and therefore the pico liter wells are merely visually observable.

It should be noted that multi-location structures can also be formed using non-embossing methods. In one example, wells can be heat and/or pressure stamped unto a suitable substrate. In another example, a plurality of elements defining picowells may be attached (e.g., using adhesive or an interference method) into wells of a multi-well device. In another example, the array is injected under pressure against a die and maintained in such manner until set.

While the above description has focused on forming picowells, other structures can be formed as well in like manner, instead of picowells and/or to support picowell operation. For example, such structures can include landmarks to assist in user orientation (e.g., patterned clusters of non-etched areas or other singularities or markings to enhance user's orientation when the array is used). Optionally, some such markings are particularly visible under a microscope (e.g., pico well address and/or a well address). In another example, micro-fluidics structures, such as reservoirs, channels, mixers, filters and flow regulators are embossed (e.g., with the embossing defining 3D structures that affect flow. Optionally or alternatively, preparation for various structures is embossed (and/or additional elements mounted on the die), for example, pumps, electronics, conductors, sensor mountings and/or valves.

The embossing process may change in accordance with the specific material or precursor used for substrate 16. For example, some materials require the application of a primer layer to strengthen the bonding to the base layer, whereas, additionally or independently, other materials require a detoxification process in order to extract biologically toxic residues such as un-cured monomers in the embossed layer.

For example, a typical precursor may be a UV-curable adhesive such as NOA-61 or NOA-81 or the low self-fluorescence NOA-63 (Norland Products Inc., Cranbury, N.J., USA, USA). Embossing is performed, for example, by applying a drop of the fluid precursor of the adhesive on glass or plastic base, and curing the fluid precursor while in contact with a die (made, for example, from a metal such as nickel, glass, PDMS or silicone rubber) having a negative geometry of the well array. The drop of adhesive disperses between the slide and the die and forms a thin layer (e.g., 10-100 micrometers thick). After the adhesive has set, the die is peeled away or otherwise removed.

Additional acts are optionally made to stabilize the structure and its adhesion to the base and/or to extract and/or remove non-polymerized residues of the adhesive which may harm cells. Such acts can include annealing at a mild temperature (~60° C.) for at least one hour. Optionally or alternatively, the bases are soaked in 90% ethanol (or other suitable solvent, depending on materials used for construction) for 5 days. This can extract toxic un-cured agents from the polymerized adhesive. Optionally or alternatively, the slides are rinsed in distilled water to wash away debris and/or residues of the extracted undesired foreign materials. Optionally or alternatively, the materials chosen and/or washing are selected to allow long term life of biological cells without toxic effects form the cell holder. Optionally, the cells reside 1 hour, 10 hours, 24 hours, 2 days, 4 days, 1 week, 1 month or more in the cell holder without such toxic effects.

Exemplary base plates for any of the embossing methods described herein include any substantially transparent glass (or plastic) surface, such as a microscope slide (0.17 mm-1 mm thick, 2.54 cm wide, 7.62 cm long), a Petri dish (either monolithic plastic dish or a plastic dish with a thin glass or polymer sheet bottom, designed for high resolution microscopy) or the bottom of microtitter plates (either monolithic plastic plate or plate having a thin glass or polymer sheet bottom, designed for high resolution microscopy).

Embossing can take place on essentially whole bottom area, or in certain areas. The size of the embossed area is determined by the applied volume of the precursor and the actual size of the die.

In some embodiments, the Petri dish or any other pico liter wells bearing device may include a partitioning element, such as a plastic or fabric barrier, to distinguish between several areas in the same device. The partitioning element, single or plural, if made or include mesh, slits or perforated parts can also act as a flow regulator, to damp and control (by selecting proper size and pitch of the openings) fluid transfer between partitions. For example, such a barrier can block or reduce fluid flow or block or reduce cellular or particle flow (e.g., of certain sizes), for example, acting as a filter. In some embodiments, the barrier serves to reduce flow rates to levels which would not remove cells/particles from picowells. Such barriers may be attached by any method known in the art. Optionally, the barriers are attached by dipping in a UV curable adhesive as used herein. Optionally, such barriers include a base ring for mechanically aligning said barriers on said substrate.

In one example, shown in FIGS. 14A-14C, For example, a cylindrical or cone mesh element 1402, made for example from Polyester or Nylon, with openings of sizes 5-10 um, or 10-50 um, or 50-100 um, or 100-200 um or 200-500 um, surrounds an embossed area 1404 (and/or is surrounded by an area 1406) in the center (or other location) of a Petri dish 1400 (or 1408). Cells are applied and settled in the embossed area wells-bearing substrate section and fluid is applied on the other side of element 1402. This can be important, for example, for keeping cells in their pico liter wells in order to reduce flow velocities and turbulence when fluid is added or taken out. Due to the restricted passage between partitions, fluid velocity is optionally reduced and/or otherwise regulated.

FIG. 13A shows a Petri dish (or other holder) 1300 having a picowell array 1304 defined in one location thereof, for example, a center, surrounded by a non-embossed region 1302. FIG. 13B is an isometric view of Petri dish 1300.

FIG. 15A shows a Petri dish (or other holder) 1500, which defines a plurality of picowell areas 1502, some or all of which are surrounded by corresponding barriers 1504.

Not all barriers need be of same type. Not all picowells or other embossed areas need be of same design and/or size. One or more optional free spaces 1506 may also be defined, with optional barriers surrounding, for example, for insertion or removal of fluids and/or for optically analyzing chemical properties of fluids.

FIG. 15B shows an alternative design 1520, having a large embossed area 1522 separated by one or more barriers 1526 from a clear area 1524. Optionally, a space 1528 is formed between the barriers.

In this and other embodiments, the coverage of the carrier by picowell and/or other embossed regions can be, for example, 1%, 5%, 10%, 20%, 50%, 70%, 90%, 100% or intermediate amounts, for example, depending on the application.

In an exemplary embodiment of the invention, multiple sizes and/or types of pico liter wells are provided on a same substrate, for example, 2, 4, 6, 10, 20 or intermediate numbers of types of pico wells may be provided.

Referring back to micro-titter plates, a pico well bearing microtitter plate can be made of, for example, a monolithic plastic structure or from a glass or transparent plastic bottom and an upper structure. In the case of a monolithic product, the die is optionally formed made as an array of "fingers" which match the pitch of the wells in the microtitter plate.

Referring specifically to FIGS. 11A-11C, a die/template may be made using the following method. As shown in FIG. 11A, a plate 1100 having a desired embossing pattern (e.g., picowells) formed thereon is covered by one or more spacers 1102, 1104 and 1106 each having one or more matching apertures 1107. Optionally, plate 1100 is made of glass or metal and spacers 1102-1106 are of silicon. FIG. 11B shows the parts assembled, at which point silicon or other setting material 1108 may be inserted into matching apertures 1107. At 11C, the top spacer 1106 is removed (or a separate base 1114 is applied over spacer 1106) and serves as a based 1114 of a template 1126. A plurality of silicone fingers 1110, with a negative embossing pattern 1112 at their tips is therefore created.

Optionally, the template is a 2D template and not a 1D template as shown for clarity.

Optionally, fingers 1110 engage spacer 1106 via inner hollows (not shown) inside spacer 1106. Optionally or alternatively, spacer 1106 is treated to adhere to the silicone and/or spacers 1104 and 1102 are treated to not adhere.

In use of such a template, precursor is optionally applied into each well, the die (1126) is then embedded in the microtitter plate and then UV radiated. The pico liter wells structure is thereby created in each well separately. Since this process is performed on ready-made monolithic plates, no leaks are expected between well areas.

Figure 12A:
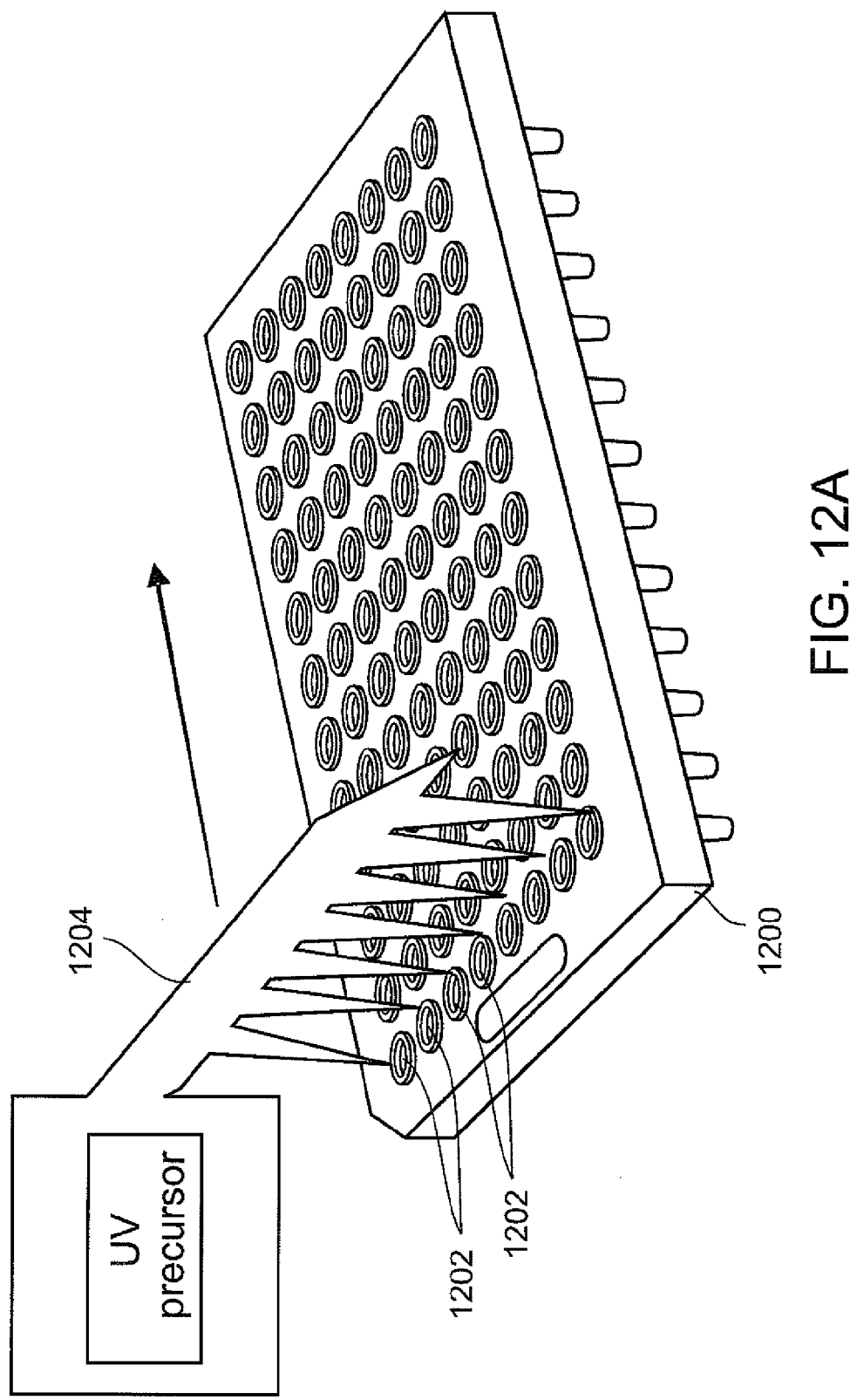
Figure 12C:
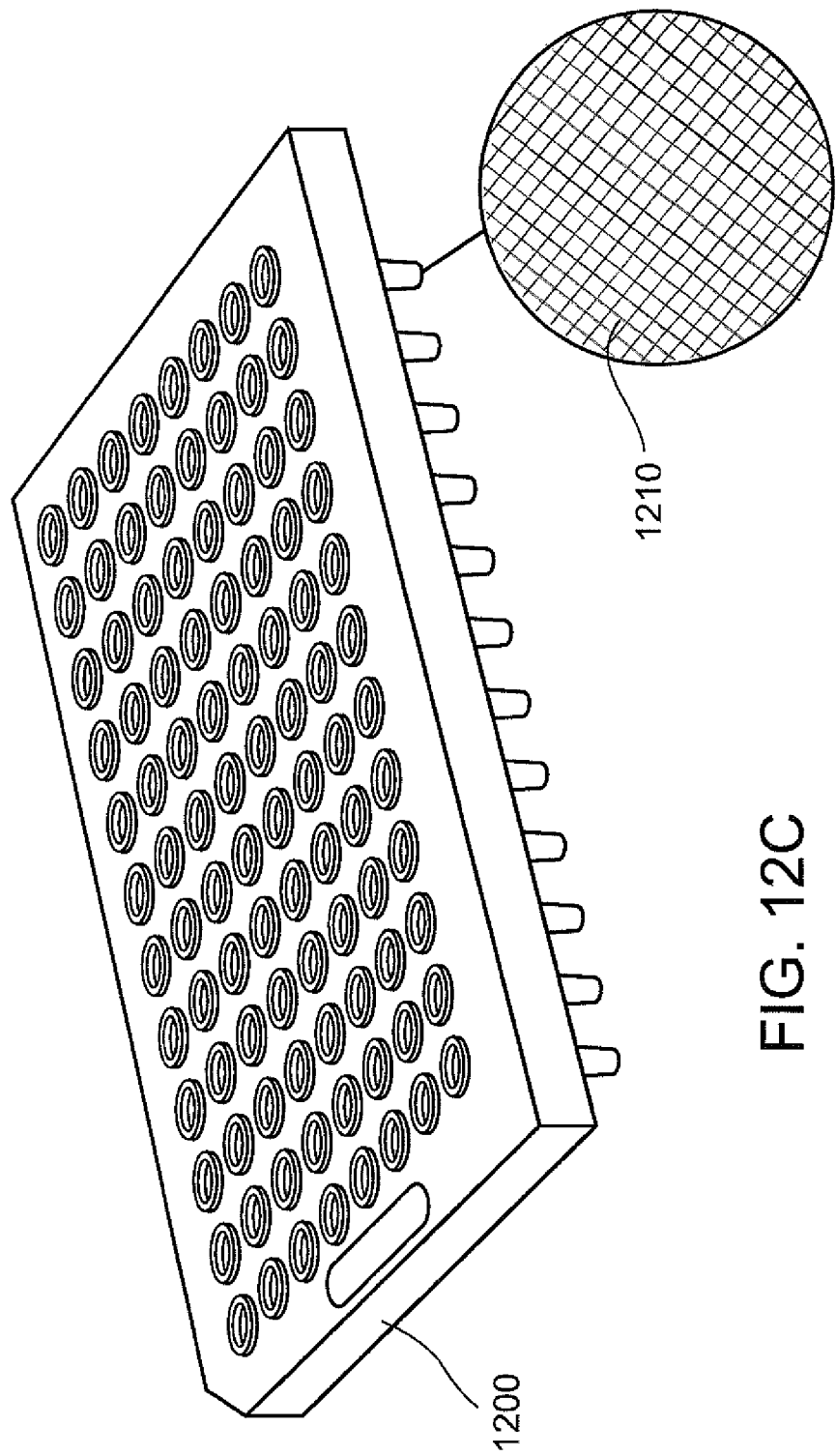

An example of this process is illustrated in FIGS. 12A-12C. In FIG. 12A, precursor material 1204 is placed in a plurality of well regions 1202 of a plate 1200, for example, using a one dimensional well filling device, for example, as known in the art of manipulating such wells with biological materials. In FIG. 12B, template 1126 (for example) is pressed into well regions 1202 and UV radiation 1208 is provided for curing. Optionally, the length of fingers 1110 is matched to the amount of precursor provided and to the clearance between template 1126 and plate 1200, so no precursor is wasted or lacking. FIG. 12C shows the result after template 1126 is removed, in which a picowell array or other embossed design 1210 is formed in those wells which were impressed by template 1126.

While all fingers 1110 are shown as being equal, this need not be the case. In one example, the fingers are of different length and define different heights for wells. Optionally or alternatively, the design at the tips 1112 is different, providing multiple well types and/or arrangements. Optionally or alternatively, the diameter of the tips is different. Optionally or alternatively, the tips emboss structures other than wells. Optionally or alternatively, the tips emboss wells of different depth. In an exemplary embodiment of the invention, for any particular application a mix of well types/sizes/number and micro fluidics constructs and fluid reservoirs is selected and made into a cell holding device. Optionally or alternatively, a plurality of "standard" such cell holder designs are made and optionally mass-produced.

In an exemplary embodiment of the invention, a non-uniform cell holder is manufactured using a configurable die. In one example, a plurality of fingers 1110 are manufactured, for example, each with a different plate 1100 having different patterns or on parts of the plate with different patterns. When needed, a die may be constructed by assembling the desired fingers in the desired arrangement to provide a template. Optionally, the fingers are reusable as they do not stick to the adhesive.

In those cases where plate consists of an upper structure and a bonded bottom, a precursor is optionally uniformly applied to the transparent bottom prior to placing the die and irradiating. Optionally, pico liter wells are created on the whole bottom area (e.g., using a flat and uniform die). The bottom plate is then bonded to the upper structure as it is usually done in this type of plates (for example, based on utilizing NOA as a cementable adhesive). Optionally or alternatively, pico liter wells may be created only at desired locations, such as those areas which will become the bottom of wells, excluding inter-wells areas. This can be controlled, for example, by applying aliquots of precursor instead of a uniform layer.

Embossing, using MY-133 or NOA or materials may be practiced on a microscope slide, either on the whole glass or selected parts and may serve as a base plate for various single or multi cavity devices. For example, the embossed glass can be covered with adhesive spacers and covers already used in laboratory practice, such as those made by Grace Biolabs (Bend, Oreg., USA) www.gracebio.com/Products/Imaging_Microscopy/CoverWell_Perfusion_Chambers and enhance the practice to include pico liter wells bottoms instead of a plain glass surface. For example, these covers can form a water-tight, multiwell cell incubation or cytochemistry chamber when pressed to coverslips or microscope slides. In some embodiments, reagents can be quickly added and removed through access ports without disturbing or cross-contaminating specimens in adjacent wells, while cells remain in their picowells.

Various devices useful for microscopy can be built based on an embossed microscope slide, for example a slide 0.17-1 mm thick. The glass is then covered with a spacing layer which has a hole just above the embossed area. The diameter of the hole may be smaller than the embossed area. This structure creates an open chamber, which can be useful for accommodating a cell suspension. This structure may be covered by a cover slip and cells can be observed by an upright and/or inverted microscope.

In another example, a slide structure supports one or more of exchanging cells media, staining, and/or other manipulations of the cells within their picowells. In such an embodiment, an additional "flow" layer is cured to form a flow channel above the cells chamber and a reservoir. This flow layer is sticky on both surfaces, thus can be bonded to the spacer layer beneath it, and to the cover layer above. Optionally, a flexible transparent cover, such as made of polycarbonate film, is bonded only on the distal edge of the flow channel. Optionally, a pinhole (or larger hole) is provided, for example, to drain air when liquids are added during the work with the device. A non-sticky removable liner is optionally provided keeps the cover from bonding to the rest of the flow channel.

Figure 16A:
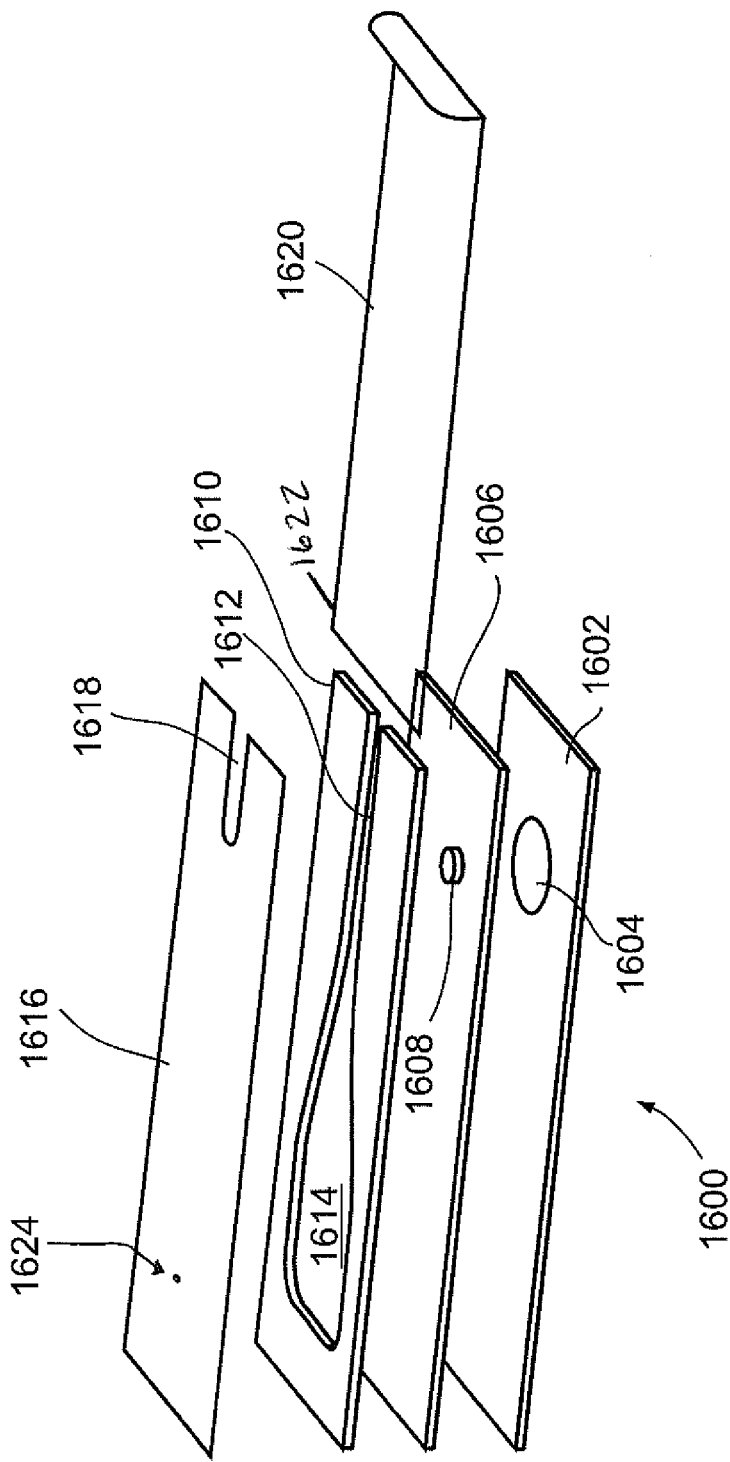
FIGS. 16A-16B illustrate a microscope slide with a pico liter well array, in a blow-apart view and in an assembled view, in accordance with an exemplary embodiment of the invention.
Figure 16B:
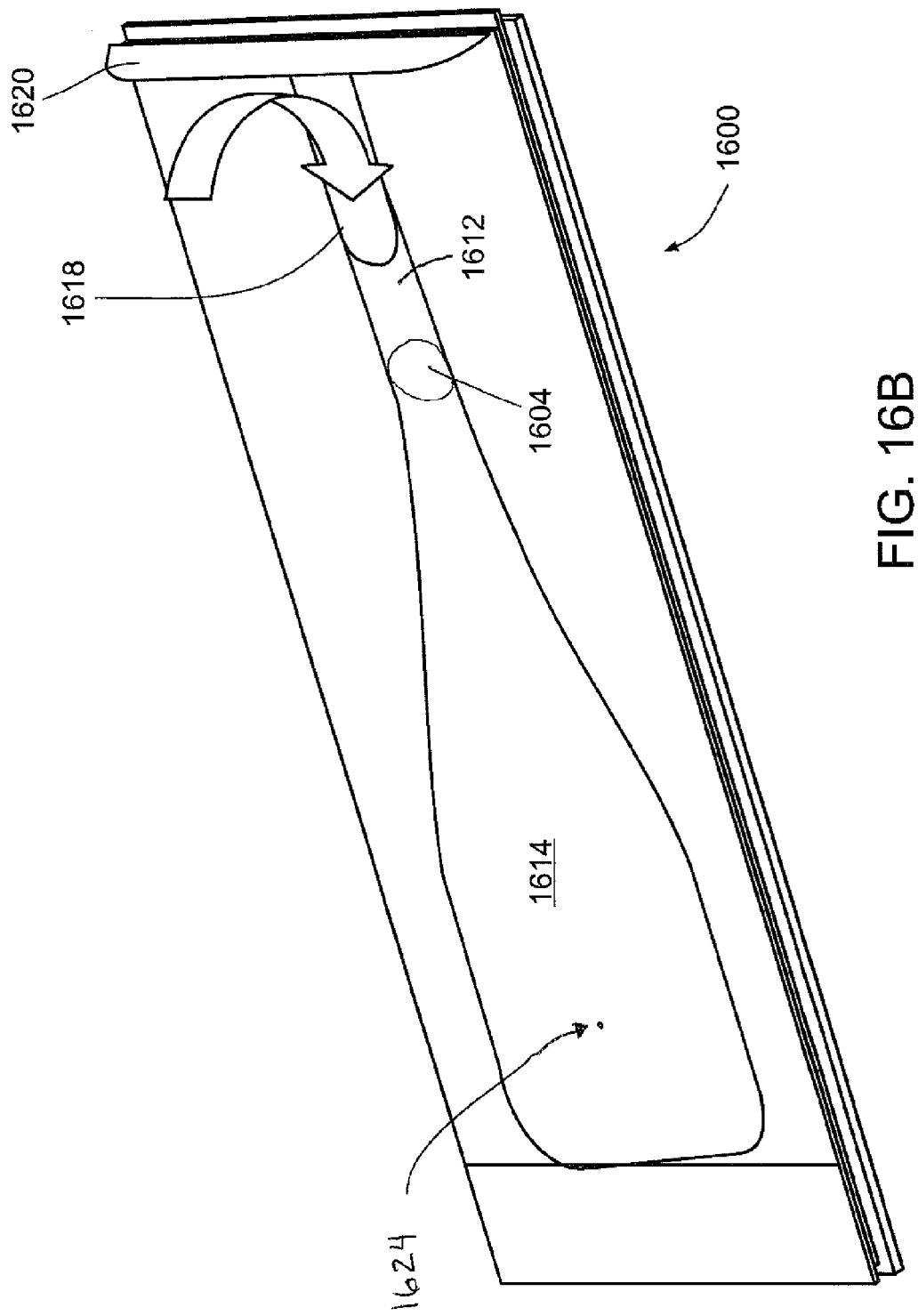

An exemplary such device 1600 is shown in FIGS. 16A and 16B, with FIG. 16A being a blow-apart view. A glass slide 1602 has embossed (or otherwise attached) thereon a picowell array 1604. A spacer layer 1606 with an aperture 1608 is attached above, for example, layer 1606 being a two sided adhesive layer. A flow layer 1610 including a flow channel 1612 and a reservoir 1614 is provided above, optionally as a two sided adhesive layer. A cover layer 1616 with an optional air hole 1624 and slot 1618 are provided above. Optionally, a non-adhesive layer 1620 is provided between layers 1616 and 1610 and includes a tip 1622 which is temporarily attached to layer 1610. Optionally, as shown in FIG. 16B, the length of layer 1620 is shorter than layers 1616 and 1610, so layers 1616 and 1610 can be adhered to each other at their tip.

Other structures may also be built up by layering shaped layers of double-sided adhesive, on microscope slides and/or other bases.

In use, flexible covers 1620 and 1616 are pulled back and expose the chamber formed by aperture 1618 and wells area 1604. Cells are loaded into the chamber and removeable liner layer 1620 is peeled off. Flexible cover 1616 is released and bonds to the rest of upper surface of flow layer 1616. Layer 1610 optionally defines a capillary channel between layers 1616 and 1606. Aliquots of fluid can be presented to the capillary slit 1618 created between the cover and the opening of the flow channel Capillary force pulls the fluid into the channel, the fluid replaces and/or flows over the cell media, and the excessive fluid is gradually accumulated in the reservoir 1614. Additional fluid can be presented to the flow channel, basically until the reservoir is full. Optionally, fluid can be removed from reservoir 1614

Double sided adhesive tapes, optionally medical grade, or other adhesive agents, may be used to bond the layers and/or to form the layers.

If double sided tapes are used, the layers are optionally bonded while wet. This can eliminate air and prevent such air from being trapping between the layers, possibly minimizing the appearance of air bubbles in the suspension along incubation time.

Optionally, the devices are manufactured and/or packed under vacuum, to prevent repeated air penetration between the layers before the device is used.

General

There has thus been described a method of making a holding device for studying cells and apparatus used in conjunction with the above described methods. Those skilled in the art will recognize that modifications may be made in the method and apparatus described herein without departing from the true spirit and scope of the invention which accordingly are intended to be limited solely by the appended claims.

It is expected that during the life of a patent maturing from this application many relevant adhesive and/or curable materials will be developed and the scope of the term adhesive is intended to include all such new technologies a priori.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method. As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of forming a cell holding device including a picoliter well array, comprising:
    (a) providing a base covered with a hardenable material, permanently adhered to said base;
    (b) contacting the hardenable material covering said base with a die, said die embossing a picoliter well region and being adapted not to adhere to said hardenable material; and
    (c) at least partially hardening said hardenable material while in contact with said die.

2. The method according to claim 1, comprising further hardening said hardenable material after removal of said die.

3. The method according to claim 1, comprising priming said base before covering with said hardenable material.

4. The method according to claim 1, comprising forming a barrier around said picoliter well region, wherein said barrier is formed on said hardening material before, during, or after said contacting.

5. A method of forming a cell holding device including a picoliter well array, comprising:
    (a) providing a base;
    (b) forming the picoliter well array in a region of said base; and
    (c) forming a barrier between said region and other parts of said base.

6. The method according to claim 5, wherein the picowell array and the barrier are formed by a die applied to said base.

7. The method according to claim 6, further including covering the base with a hardenable material before application of the die; and fully curing said hardenable material before removal of said die to form a permanent layer on the base.

8. The method according to claim 7, wherein the hardenable material is UV-light curable.

9. The method according to claim 5, wherein the barrier is formed before the picowell array.

10. The method according to claim 5, wherein the barrier and the picowell array are formed at the same time.

11. The method according to claim 5, wherein the barrier is formed after the picowell array.

12. The method according to claim 5, wherein the base is a Petri dish.

13. The method according to claim 12, wherein the barrier is formed by a plastic ring.

14. The method according to claim 5, wherein the barrier is formed by a separate element attached to the base.

15. The method according to claim 14, wherein the barrier is formed by a plastic ring.

* * * * *